United States Patent [19]
Krimpenfort et al.

[11] Patent Number: 5,591,669
[45] Date of Patent: * Jan. 7, 1997

[54] TRANSGENIC MICE DEPLETED IN A MATURE LYMPHOCYTIC CELL-TYPE

[75] Inventors: Paulus J. A. Krimpenfort, Amsterdam; Antonius J. M. Berns, Spaarndam, both of Netherlands

[73] Assignee: GenPharm International, Inc., Palo Alto, Calif.

[ * ] Notice: The term of this patent shall not extend beyond the expiration date of Pat. No. 5,175,384.

[21] Appl. No.: 454,034

[22] Filed: May 30, 1995

Related U.S. Application Data

[63] Continuation of Ser. No. 919,936, Jul. 27, 1992, Pat. No. 5,434,340, which is a continuation of Ser. No. 280,218, Dec. 5, 1988, Pat. No. 5,175,384.

[51] Int. Cl.$^6$ .................................................. C12N 15/00
[52] U.S. Cl. ..................... 800/2; 800/DIG. 1; 435/172.3; 935/111
[58] Field of Search .................................. 800/2, DIG. 1, 800/DIG. 2, DIG. 3; 435/172.3, 320.1, 317.1; 935/111

[56] References Cited

U.S. PATENT DOCUMENTS

| | | | |
|---|---|---|---|
| 5,175,384 | 12/1992 | Krimpenfort et al. | 800/2 |
| 5,434,340 | 7/1995 | Krimpenfort et al. | 800/2 |

OTHER PUBLICATIONS

J. Chen et al., "Immunoglobulin gene rearrangement in B cell deficient mice generated by targeted deletion of the $J_H$ locus," *International Immunology* 5(6), 647–656 (1993).

D. Corcos et al., "Allelic exclusion in transgenic mice expressing a heavy chain disease–like human μ protein," *Eur. J. Immunol.* 21, 2711–2716 (1991).

R. Fenton et al., "Isotypic exclusion of γδ T cell receptors in transgenic mice bearing a rearranged β–chain gene," *Science* 241, 1089–1092 (Aug., 1988).

L. Herzenberg et al., "Depletion of the predominant B–cell population in immunoglobulin μ heavy–chain transgenic mice," *Nature* 329, 71–73 (Sep. 3, 1987).

A. Kantor et al., "Origin of Murine B Cell Lineages," *Annual Review of Immunology* 11, 501–529 (1993).

M. Nussenzweig et al., "Allelic exclusion in transgenic mice that express the membrane form of immunoglobulin μ," *Science* 236, 816–818 (May, 1987).

A. Stall et al., "Rearrangement and expression of endogenous immunoglobulin genes occur in many murine B cells expressing transgenic membrane IgM," *Proc. Natl. Acad. Sci. USA* 85, 3546–3550 (May, 1988).

Y. Uematsu et al., "In transgenic mice the introduced functional T cell receptor β gene prevents expression of endogenous β genes," *Cell* 52, 831–841 (Mar 25, 1988).

Sakano et al Nature 286: 676, 1980.
Choi et al Nature 286: 776, 1980.
Sakano et al Nature 280: 288, 1979.
Seedman et al Nature 286: 779, 1980.
Max et al PNAS 76: 3450, 1979.
Orkin et al PNAS 78: 5041, 1981.
Miller et al Nature 295: 428, 1982.
Treisman et al Nature 302: 591, 1983.
Chen et al International Immunology 5(6): 647, 1993.

*Primary Examiner*—Jasemine C. Chambers
*Attorney, Agent, or Firm*—Townsend and Townsend and Crew LLP

[57] ABSTRACT

Transgenic mice having a phenotype characterized by the substantial depletion of a mature lymphocytic cell type otherwise naturally occurring in the species from which the transgenic mouse is derived. The phenotype is conferred in the transgenic mouse by a transgene contained in at least the precursor stem cell of the lymphocytic cell type which is depleted. The transgene comprised is a DNA sequence encoding a lymphatic polypeptide variant which inhibits maturation of the lymphocytic cell type.

5 Claims, 16 Drawing Sheets

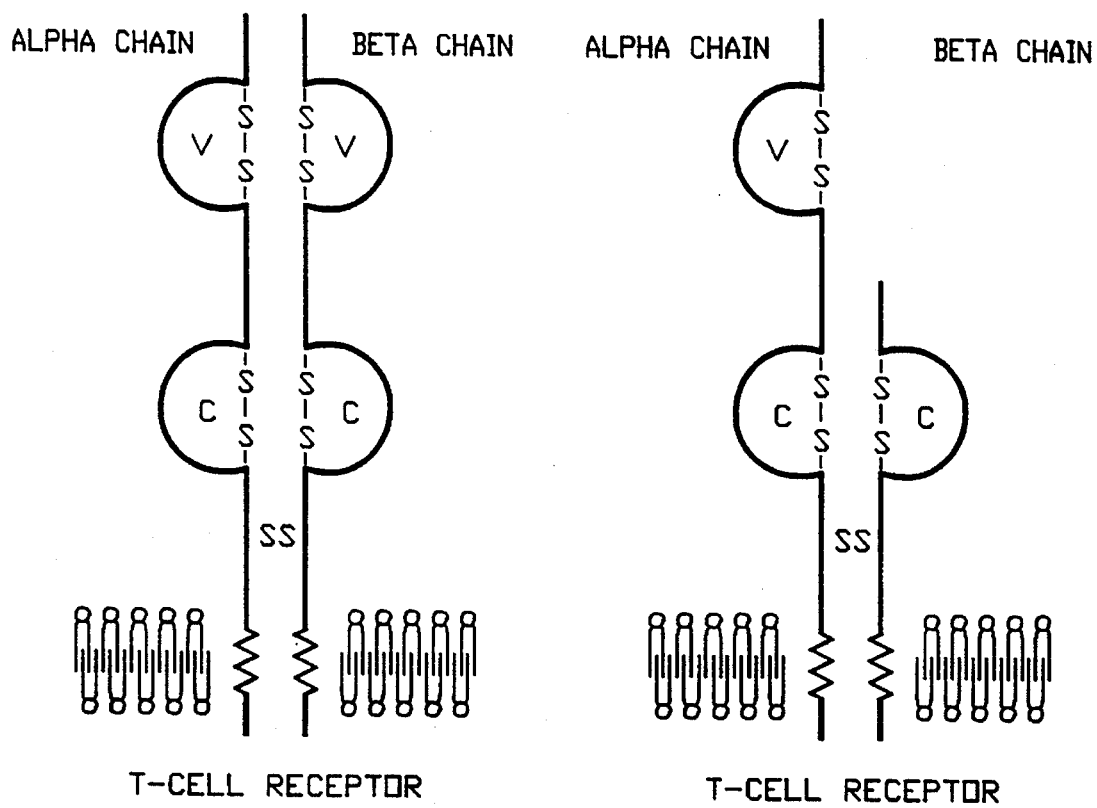
FIG.—1A   FIG.—1B
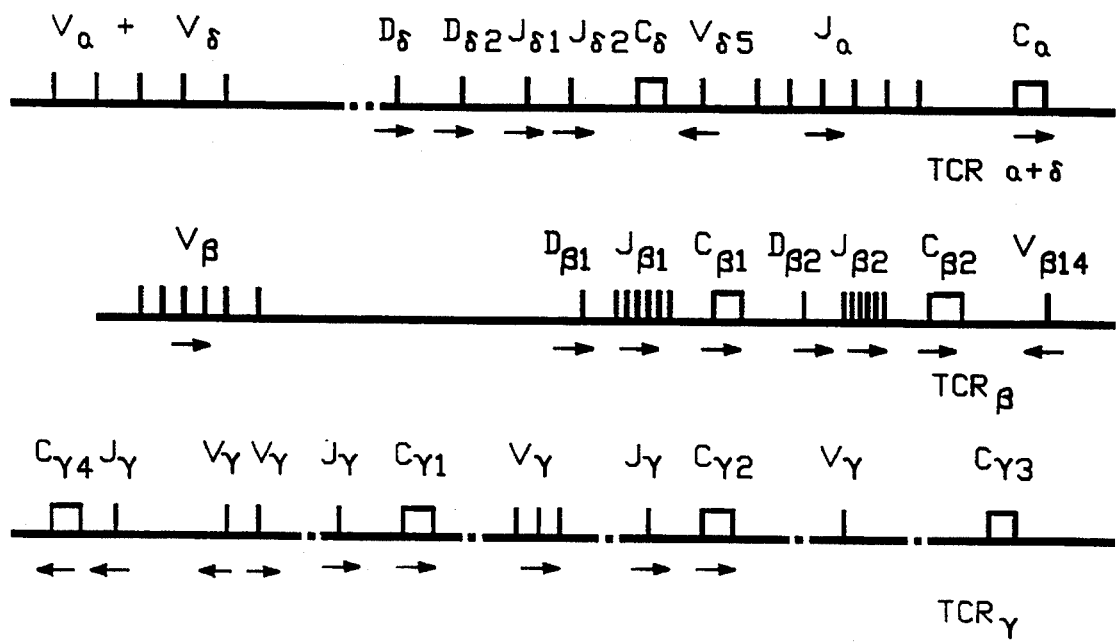
FIG.—2

```
AAGAGGACTTTCCCACACCCAGCCCTATTTACTCAATACAGCCATCTCCCCTTCTATTGA    60
GAAGGAAAAGGGCTGAGACTAAGGTCCAGTACTACAGAGAGCCTAGTGGGAGTAACAGTA   120
TCAACAGATCACTGACCTCAGAATCTGACATCACAGGCAATGATGATAGGAGGAGAAAGG   180
                                   5'UT ←—|—→ L5.1
AGGAGCTGACTCCTGCTCTCTCACCAAAGAGACCATATCCTAGAGGAAGCATGTCTAACA   240
CTGCCTTCCCTGACCCGCCTGAACACCACCCTGCTATCTTGGGTTGCTCTCTTTCTCC    300
    |—→ VB8.2
TGGGAACAAAACACATGGAGGCTGCAGTCACCCAAAGCCCAAGAAACAAGGTGGCAGTAA   360
CAGGAGGAAAGGTGACATTGAGCTGTAATCAGATAATAACCACAACAACATGTACTGGT   420
ATCGGGCAGGACACGGGGCATGGGCTGAGGCTGATCCATTATTCATATGGTGCTGGCAGCA   480
CTGAGAAAGGAGATATCCCTGATGGATACAAGGCCTCCAGACCAAGCCAAGAGAACTTCT   540
                                                        DB2
                                                    ←—|
CCCTCATTCTGGAGTTGGCTACCCCCTCTCAGACATCAGTGTACTTCTGTGCCAGGGGTG   600
    |—→ JB2.3
ATAACAGTGCAGAAAACGCTGT                                          620
```

FIG. —3A

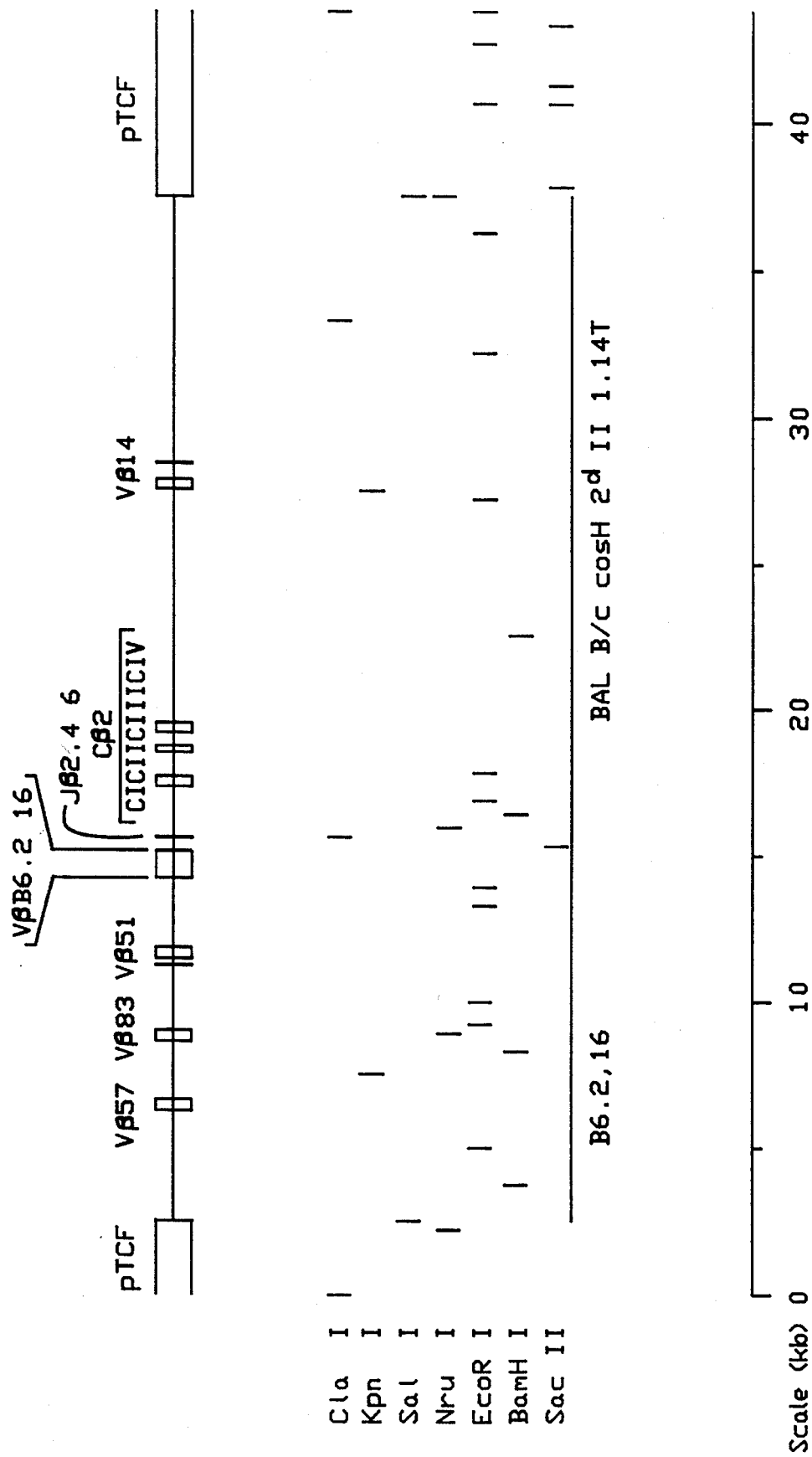
FIG.—3B

| Cells | B6.2.16 | | | C57bl/6 | | | 93.2 | | |
|---|---|---|---|---|---|---|---|---|---|
| preclearing | − | + | + | − | + | + | − | + | + |
| anti-beta | + | − | + | + | − | + | + | − | + |
| F23.1 | − | + | − | − | + | − | − | + | − |

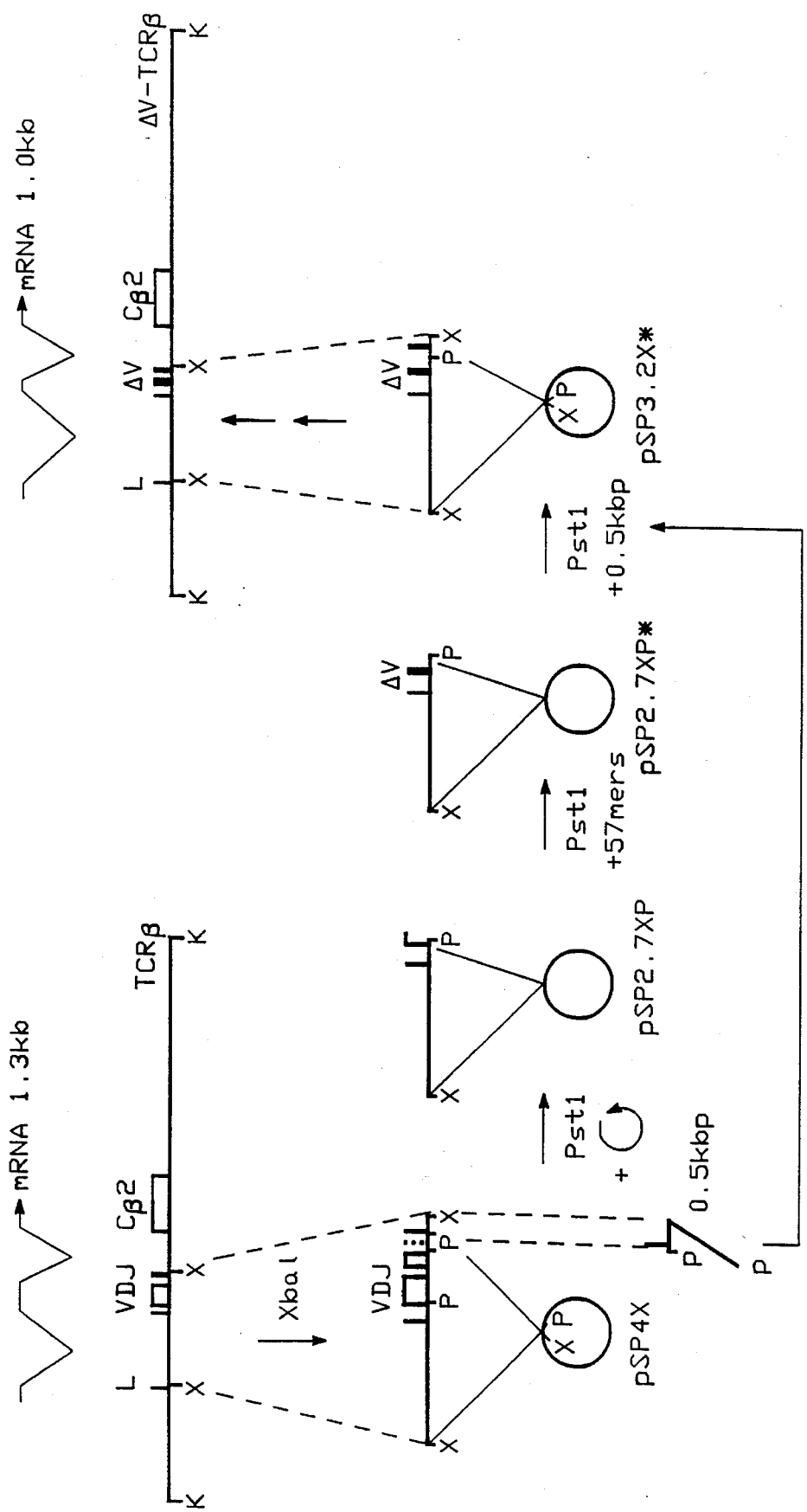
FIG.—11A

```
                                                 103 AMINO ACIDS 0.65 KBP

LYS HIS MET GLU ALA ALA   THR ARG LEU THR VAL LEU G
TTTATTATAG    AA CAC ATG GAG GCT GCA   ACC AGA CTG ACT GTT CTC G   GTAAGTTGGGAGCTAGTAAT
SPLICE                  Vβ8.2                          Jβ2.3                 SPLICE
ACCEPTOR                                                                     DONOR

ACC AGA CTG GAC TGT TCT CG  GTAAGTTGGGAGCTAGTAAT
                                                         ↑
```

FIG.-11B

| FIG.-11B | FIG.-11B' |

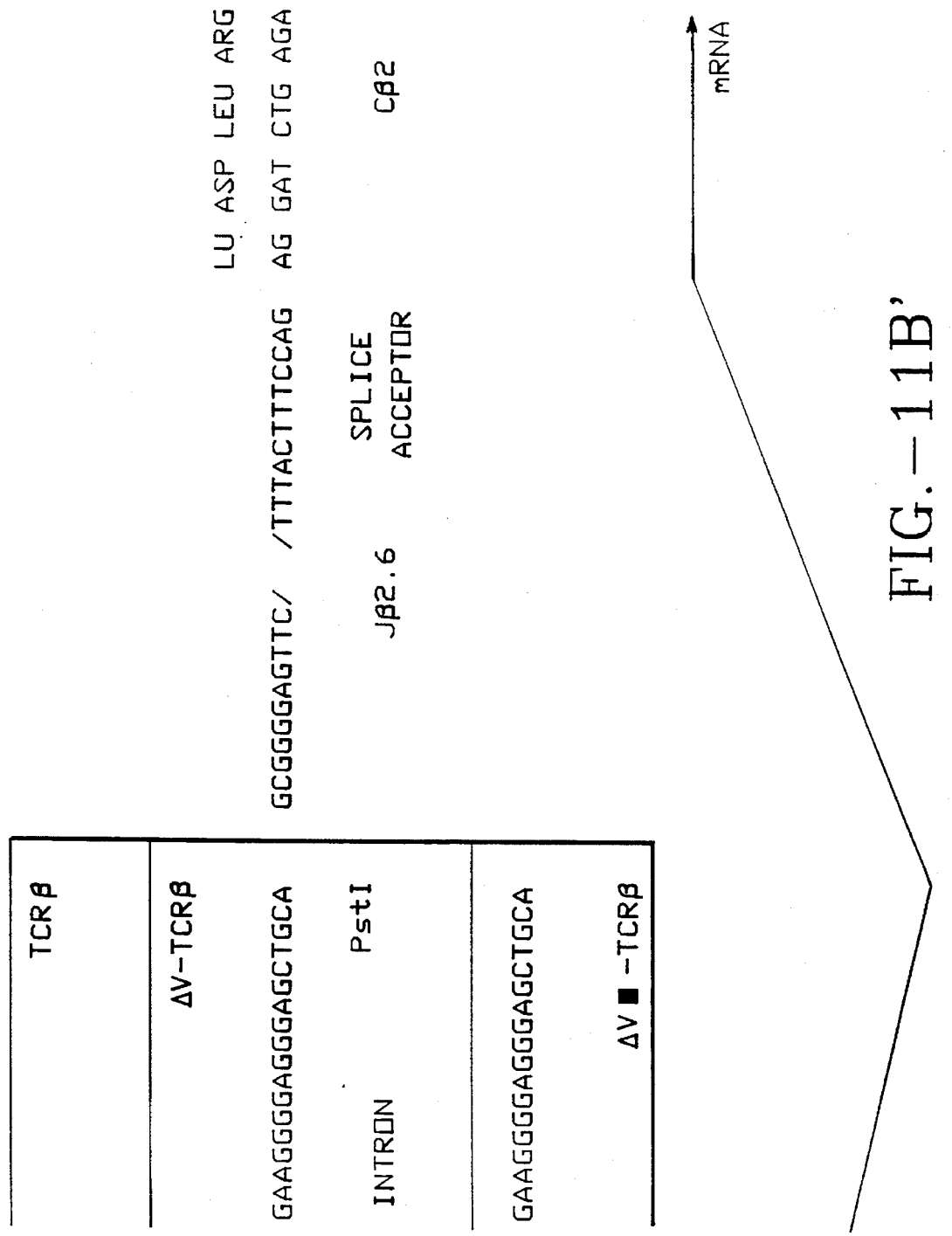
FIG.—11B'

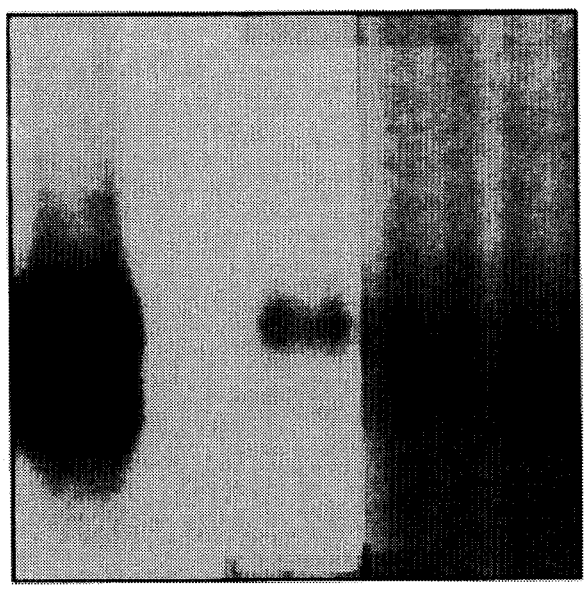
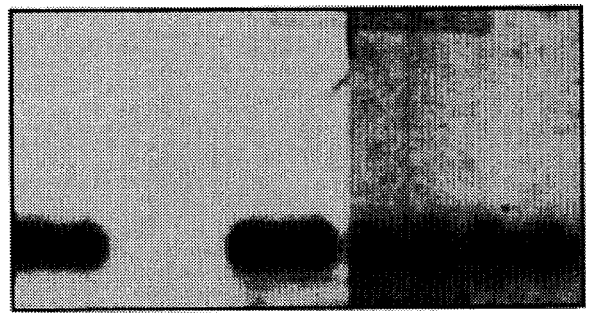
FIG. 13

FIG.-15A mRNA start

AAGAGGACTTTCCCACACCCAGCCCTATTTACTCAATACAGCCATCTCCCCTTCTATTGA
GAAGGAAAAGGGCTGAGACTAAGGTCCAGTACTACAGAGAGCCTAGTGGGAGTAACAGTA
TCAACAGATCACTGACCTCAGAATCTGACATCACAGGCAATGATGATAGGAGGAGAAAGG
                                                                                             L5.1
                                                 5'UT-| M S N
AGGAGCTGACTCCTGCTCTCTCACCAAAGAGACCATATCCTAGAGGAAGC ATGTCTAAC
 T A F P D P A W N T L L S W V A L F L
ACTGCCTTCCCTGACCCGCCTGGAACACCACCCTGCTATCTTGGGTTGCTCTCTTTCTC
   ↑Vβ8.2
 L G T K H M E A A V T Q S P R N K V A V
CTGGGAACAAAACACATGGAGGCTGCAGTCACCCAAGAGCCCAAGAACAAGGTGGCAGTA
 T G G K V T L S C N Q T N N H N N M Y C
ACAGGAGGAAAGGTGACATTGAGCTGTAATCAGACTAATAACCACAACATGTACTGG
 Y R A D T G H T L R L I H Y S Y G L G S
TATCGGGCAGGACACGGGCATGGCCTGAGGCTGATCCATTATTCATATGGTGTGGCAGC
 T E K G D I P D G Y K P S R P S Q E D F
ACTGAGAAAGGAGATATCCCTGATGGATACAAGGCCTCCAGACCCAGCCAAGAGACTTC
                                                                                    |→Dβ2
 S L I L E L A T P S Q T S V Y F C A S  G
TCCCTCATTCTGGAGTTGGCTACCCCTCAGACATCAGTGTACTTCTGTGCCAGCGGT
 |→Jβ2.3                         ↑C
 D N S A E T L Y F G S G T R L T V L E D
GATAACAGTGCAGAAACGCTGTATTTGGCTCAGGAACCAGACTGACTGTTCTCGAGGAT
 L R N V T P P K V S L F E P S K A E I A
CTGAGAAATGTGACTCCACCCAAGGTCTCCTTGTTTGAGCCATCAAAGGCAGAGATTGCA
 N K Q K A T L V C L A R G F F P D H V E
AACAAACAAAAGGCTACCCTCGTGTGCTTGGCCAGGGGCTTCTTCCCTGACCACGTGGAG

FIG.—15B

```
 L  S  W  V  N  G  K  E  V  H  S  G  V  S  T  Q  P  Q  A
CTGAGCTGGTGGGTGAATGGCAAGGAGGTCCACAGTGGGGTCAGTGGGACCCTCAGGCC
 V  K  E  S  N  Y  S  Y  C  L  S  R  L  R  V  S  A  T  F
TACAAGGAGAGCAATTATAGCTACTGCCTGAGCAGGCTGAGGGTCTCTGCTACCTTC
 W  H  N  P  R  N  H  F  R  C  Q  V  Q  F  H  G  L  S  E  E
TGGCACAATCCTCGAAACCACTTCCGCTGCCAAGTTCCAGTTCCATGGGCTTCAGAGGAG
                                       ↑
                                       CP
 Q  K  W  P  E  G  S  P  K  P  V  T  Q  N  I  S  A  E  A  W
GACAAGTGGCCAGAGGGCTCACCCAAACCTGTCACACAGAACATCAGTGCAGAGGCCTGG
 G  R  A
GGCCGAGCAGGTAAGTGCGAGCTCATGAGGAAAGTAAACAGCACTAGTACTTCAAAAAA
TATGAAACAATCCATGTAGAAGTGAAGAATAGACCCAGGAAAAGGCCAGAGTGGTGGGAC
AGATAGTCAAGCTCATGGTGTCAGAAAACCATAGCCTATGTCTTCCTCCAAGGAGTATGT
ATGTAAACTCAGTGGGGCAGCTCAGGCCAATTGGCTTCCCAGTTCTTTAGTGTCTCAGAG
CTGTGCTTAAGAGGGTCTCCCATACCCTCACAACCTAGCATCGCTCATCCCCATCCCT
GCTGCTAGAGGGTCACTCTGACAGTGTCGTATAACCATCTGACATGCATGTGTCTGTG
AGACAGTGTGAGGACTATAAGAGGAGAGTGCTTACACACCTGCTTACACACAGAATCAGAA
GCCTTTACATTGGGCTTTAAGTTTTGTTGTTGGGTGTTCAATGTCCCCAAAGTGGCTTT
                                     D  C  G  I  T  S
CTTTCACCCAATTTCTCCCTCTCCTTTCTTTCA   GACTGTGGAATCACTTCAGGTGAG
TAGATCTTCCGACTTTCTCTACGTCTTCTGTGGTCTTGAAAACAGGACACAAAT
ATCCTATAGACATGAGGGTCGGAGGCTGCCCAGGAACTAGCTCACAAACACCTAAC
                      A  S  Y  H  Q  G  V  L  S  A  T  I  L  Y
TCTCCTTTCCTGTCAACAGCATCCATCATCAGGGGTTCTGTCTGCAACCATCCTCTAT
 E  I  L  G  K  A  T  L  Y  A  V  L  V  S  G  L  V  L  N
 ↑TM
GAGATCCTACTGGGGAAGGCCACCCTATATGCTGTGCTGGTCAGTGGCCTGGTGCTGATG
```

FIG.–15C

```
         A   N
         GCCATGGTAAGAATGGTAGGATGGACAAATGGTTGGAGGGATAGACTGCAGTGTATGGAT
         ATAAAGGGATCTCAGAGAGGAGGACCCAGCCCTGATATCCTGCCATTTCAAAAAAGACCATA
         AAAAACACAGTGCAAAGCAAAAACACAGGAATGCTTATGTTTGTACTCCTGGAAGATGAA
         GAGAACCAAGGAGCTCTCTTCAAGATCATACTTGAAAAATCCCTTTTTGTATCCCCTTCC
                                                                    Cy
                                                               V  K  K
         CTCTGCTCCATGGATTCTGGGAGGTCTAACAATGTCTTCTCTTCTTCTCAGGTCAAGAAAAAA
         N    3'UT
         N  S
         AATTCCTGAGACACAAACTTTTATGCATCCTGAGCCGTTCTTCACCCTGGCCATAGATTTTC
         CTGCACCTTCTCTAATTCCTGTTCCTAAGAACTTGTCTCTTCCTCCATGGATATCCA
         TCCTTCCCTCGTTGACACCTTCACTCTGAAACAGACTAAATCAATAAAAACATGGAGTTAA
         CCTGGTTGTGTCTCAGCAGTTTCTTTGGACTTCCTGTGGTTACTGACATTCCTACTGGTCT
         GAAAAGGCAAACAGAATGACTAATCTGCCTTCTGTCTGAAGGGCAATGACTGGACTCCGACAGGATA
         ACTTTAGATCCTCCAATGAGTCATTTGTCTGAAGGGCAATGACTGGACTCCGACAGGATA
         AAGACAGAGAAAGAAAAATTACCACTAACAATAACCCCACCAGTATAGGACAGAAGCTA
         AGCAGACCTATTTAATTCTCAATTACAGAGTCCAGTTCTTTTGTTTCAACTTCAGATTT
         TATCTGTATCTCCCTCAATATCTCTGGCTTATCTTGTTTGAAAGCTT
```

TRANSGENIC MICE DEPLETED IN A MATURE LYMPHOCYTIC CELL-TYPE

This is a Continuation of application Ser. No. 07/919,936 filed Jul. 27, 1992, now U.S. Pat. No. 5,434,340, which is a Continuation of Ser. No. 07/280,218, filed Dec. 5, 1988, now U.S. Pat. No. 5,175,384.

FIELD OF THE INVENTION

The present invention relates to transgenic non-human animals wherein the mature form of at least one lymphocytic cell type is substantially depleted. More particularly, the invention relates to transgenic mice wherein mature T cells or plasma cells are depleted.

BACKGROUND OF THE INVENTION

The immune response is a complex defense system that is able to recognize and kill invading organisms such as bacteria, viruses, fungi and possibly also some types of tumor cells. The most characteristic aspects of the immune system are the specific recognition of antigens, the ability to discriminate between self and non-self antigens and a memory-like potential that enables a fast and specific reaction to previously encountered antigens. The vertebrate immune system reacts to foreign antigens with a cascade of molecular and cellular events that ultimately results in the humoral and cell-mediated immune response.

The major pathway of the immune defense commences with the trapping of the antigen by accessory cells such as dendritic cells or macrophages and subsequent concentration in lymphoid organs. There, the accessory cells present the antigen on their cell surface to subclasses of T cells classified as mature T helper cells. Upon specific recognition of the processed antigen the mature T helper cells can be triggered to become activated T helper cells. The activated T helper cells regulate both the humoral immune response by inducing the differentiation of mature B cells to antibody producing plasma cells and control the cell-mediated immune response by activation of mature cytotoxic T cells.

Naturally occurring processes sometimes result in the modulation of immune system cell types. Acquired immunodeficiency syndrome (AIDS) is a devastating infectious disease of the adult immune system which significantly affects cell-mediated immunity. This disease is manifested by profound lymphopenia which appears to be the result of a loss of T-lymphocytes which have the helper/inducer phenotype T4 as defined by the monoclonal antibody OKT4 (Fauci, A., et al. (1984) *Annals. Int. Med.* 100, 92). Other clinical manifestations include opportunistic infections, predominantly *Pneumocystis carinii* pneumonia, and Karposi's sarcoma. Other disease states include Severe Combined Immuno Deficiency Syndrome (SCID) wherein T, B or both cell types may be depleted in humans. It is the existence of diseases affecting the immune system, such as AIDS and SCID, which has created the need for animal model systems to study the epitology and potential treatment of such disease states.

T lymphocytes recognize antigen in the context of self Major Histocompatibility Complex (MHC) molecules by means of the T cell receptor (TCR) expressed on their cell surface The TCR is a disulfide linked heterodimer noncovalently associated with the CD3 complex (Allison, J. P., et al. (1987) *Ann. Rev. Immunol.* 5, 503). Most T cells carry TCRs consisting of α and β glycoproteins. T cells use mechanisms to generate diversity in their receptor molecules similar to those operating in B cells (Kronenberg, M., et al. (1986) *Ann. Rev. Immunol.* 4, 529; Tonegawa. S (1983) *Nature* 302, 575). Like the immunoglobulin (Ig) genes, the TCR genes are composed of segments which rearrange during T cell development. TCR and Ig polypeptides consist of amino terminal variable and carboxy terminal constant regions. The variable region is responsible for the specific recognition of antigen, whereas the C region functions in membrane anchoring and in transmitting of the signal that the receptor is occupied, from the outside to the inside of the cell. The variable region of the Ig heavy chain and the TCR β chain is encoded by three gene segments, the variable (V), diversity (D) and joining (J) segments. The Ig light chain and the TCR α chain contain variable regions encoded by V and J segments only.

The V, D and J segments are present in multiple copies in germline DNA. The diversity in the variable region is generated by random joining of one member of each segment family. Fusion of gene segments is accompanied by insertion of several nucleotides. This N-region insertion largely contributes to the diversity, particularly of the TCR variable regions (Davis and Bjorkman (1986) *Nature* 334, 395), but also implies that variable gene segments are often not functionally rearranged. The rearrangement of gene segments generally occurs at both alleles. However, T and B cells express only one TCR or Ig respectively and two functionally rearranged genes within one cell have never been found. This phenomenon is known as allelic exclusion.

During B cell development the rearrangement process starts at both heavy chain gene alleles. First a D segment is fused to a J segment followed by ligation of a V segment to the DJ join. If the VDJ joining is productive, further rearrangement of the other heavy chain allele is blocked, whereas rearrangement of the light chain loci is induced (Reth, M., et al. (1985) *Nature* 517, 353).

In both B and T cells, partially (DJ) and completely (VDJ) rearranged genes reportedly are transcribed giving rise to two differently sized RNA molecules (Yancopoulos, G., et al. (1986) *Ann. Rev. Immunol.* 4, 339; Born, W., et al. (1987) *TIG* 3, 132). In B cells the DJ transcripts can be translated into a Dµ-chain, a truncated form of the Igµ heavy chain that lacks a V segment derived sequence. In general, the Dµ-chain is present in minor amounts, if at all. However, in one subclone (P4-11) of the 300-19 cell line, a transformed pre-B cell line which differentiates in vitro to Ig producing B cells, the expression of the Dµ-chain is reportedly very high (Reth, M., et al. (1985) *Nature* 317, 353). This reference also reports that the heavy chain gene alleles in the P4-11 clone are blocked at the DJ rearrangement stage in cell culture and that such cells show a very high frequency of light chain gene rearrangements. This has led to the suggestion that the Dµ protein contains some of the regulatory determinales necessary for gene assembly (Yancopoulos, G., et al. (1986) *Ann. Rev. Immunol.* 4, 339, 356).

Transgenic mice containing functionally rearranged Ig genes reportedly have been used in studying several aspects of Ig gene expression, e.g. tissue specific expression, the mechanism of segment rearrangement, allelic exclusion and repertoire development (Storb, U. (1987) *Ann. Rev. Immunol.* 5, 151). It has also been reported that the transgenic heavy chain polypeptide only inhibits the complete VDJ rearrangement of endogenous heavy chain genes if it contains a transmembrane domain (Storb, 1987; Iglesias, A., et al. (1987) *Nature* 330, 482; Nussenzweig, M., et al. (1987) *Science* 236, 816; Nussenzweig, M., et al. (1988) *J. Exp. Med.* 167, 1969).

Recently, the inventors reported that functionally rearranged TCRβ genes can be appropriately expressed in transgenic mice (Krimpenfort, P., et al. (1988) *EMBO* 7, 745). This functional TCRβ chain gene prevents expression of endogenous β genes by inhibiting complete VDJ joining (Uematsu, Y., et al. (1988) *Cell* 52, 831).

Two different types of T cells are involved in antigen recognition within the self MHC context. Mature T helper cells (CD4$^+$CD8$^-$) recognize antigen in the context of class II MHC molecules, whereas cytotoxic T cells (CD4$^-$CD8$^+$) recognize antigen in the context of class IMHC determinants (Swain, S. L. (1983) *Immun. Rev.* 74, 129–142; Dialynas, P. D., et al. (1983) *Immun. Rev.* 74, 29–56). It has been reported that class II-specific CD4$^+$CD8$^-$ helper T cells (also referred to as T4 cells) fail to develop in mice neonatally treated with anti-class II MHC monoclonal antibody (Kruisbeek, A. M., et al. (1983) *J. Exp. Med.* 157, 1932–1946; Kruisbeek, A. M., et al. (1985) *J. Exp. Med.* 161, 1029–1047). Similarly, it has recently been reported that mice chronically treated with anti-class I MHC monoclonal antibody from birth have a significantly reduced population of CD4$^-$CD8$^+$ cells and cytotoxic T cell precursors (Marusic-Galesic, S., et al. (1988) *Nature* 333, 180–183). Although selected T cell populations apparently can be produced by such methods, continuous administration of antibody is required which often results in adverse side effects in such mice.

A different strategy to deplete specific cell lines has recently been identified wherein specific cell destruction is induced by administration of a toxic metabolite. Specifically, transgenic mice reportedly were produced containing a Herpes Simplex Virus Thymidine Kinase (HSV-TK) transgene fused to the Ig promoter/enhancer. Transgenic cells that express the HSV-TK are not affected. However, upon administration of a nucleoside analog that can be phosphorylated by the transgenic HSV-TK gene, replicating cells expressing the HSV-TK gene are killed (Heyman, et al. (1988) *UCLA Symposia on Molecular and Cellular Biology*, 73, 199.

Another approach to depletion of specific cell types has been reported using tissue specific expression of a bacterial toxin. Specifically, mice carrying an elastase/diptheria toxin A (DT-A) fusion gene lacked a normal pancreas (Palmeter, et al. (1987) *Cell* 50, 435). In addition, it has been reported that microphtalmia in transgenic mice resulted from the introduction of the DT-A gene fused to the α2-crystallin promoter (Bretman, et al. (1987) *Science* 238, 1563).

Transgenic mice reportedly have also been constructed that express an αβBTCR in a large fraction in their T cells which is specific for a minor histocompatibility antigen (H-Y) present on male, but not female, cells (Kisielow, P., et al. (1988) *Nature* 333, 742–746). This very recent reference reports that cells containing the TCR for the H-Y antigen were frequent in female but not in male transgenic offspring. The αβ TCR in such trasgenic mice apparently contains all the segments and regions required for a functional TCR.

The references discussed above are provided solely for the disclosure prior to the filing date of the present application and nothing herein is to be construed as an admission that the inventors are not entitled to antedate such disclosures by virtue of prior invention.

Given the state of the art, it is apparent that a need exists for animal model systems to study diseases which effect the immune system including infectious diseases such as AIDS. Accordingly, it is an object herein to provide transgenic non-human animals and methods for making the same which have a phenotype characterized by the substantial depletion of a mature lymphocytic cell type otherwise naturally occurring in the species from which the transgenic is derived.

It is also an object herein to provide transgenic non-human animals substantially depleted in mature T cells or plasma cells.

It is a further object herein to provide transgenic mice substantially depleted in mature T cells or plasma cells.

Still further, it is an object herein to provide transgenes capable of producing such transgenic non-human animals.

Further, it is an object herein to provide methods for producing transgenic non-human animal having at least one of the above identified phenotypes.

SUMMARY OF THE INVENTION

The invention is based on the discovery that transgenic non-human animals depleted in a lymphatic cell type can be produced by disrupting the expression of a functional lymphocytic polypeptide required for maturation of the lymphocytic cell type. This lymphocytic polypeptide is otherwise expressed by the non-human animal from which the transgenic animal is derived.

In one aspect, the invention provides transgenic non-human animals having a phenotype characterized by the substantial depletion of a mature lymphocytic cell type otherwise naturally occurring in the species from which the transgenic animal is derived. This phenotype is conferred in the transgenic animal by a transgene contained in at least the precursor stem cell of the lymphocytic cell type which is depleted. The transgene comprises a DNA sequence encoding a lymphatic polypeptide variant which inhibits formation of the depleted lymphocytic cell type. Generlly, such inhibition occurs when the lymphatic polypeptide variant is expressed in a precursor to the lymphocytic cell type.

In those cases where the lymphatic polypeptide variant is expressed, the variant is believed to be capable of suppressing expression of at least one set of cognate endogenous alleles normally expressed during differentiation of the precursor stem cell to the mature lymphocytic cell type. The lymphatic polypeptide variant, however, lacks a functional domain necessary for maturation of the lymphocytic cell type which would otherwise be provided by either or both of the suppressed endogenous alleles.

Within the context of transgenic animals deficient in T cells, the transgene encodes a lymphatic polypeptide variant comprising a portion of a TCRβ chain. The transgene encoding the TCRβ variant chain typically retains sequences encoding at least the transmembrane sequence found in the C region of a naturally occurring TCRβ chain. This sequence may be operably linked to an appropriate signal sequence. It lacks, however, sequences encoding all or part of the variable region. The C region contained by such a lymphatic polypeptide variant is capable of suppressing the expression of endogenous TCR alleles thereby preventing the membrane expression of functional heterodimeric TCRs. Normal T cell maturation is thereby abrogated.

In the case of non-human transgenic animals substantially depleted in antibody secreting plasma cells, the transgene similarly encodes a lymphatic polypeptide variant containing at least the transmembrane sequence of the C region of the Ig heavy chain. A signal sequence may also be operably linked to the transgene encoding the lymphatic polypeptide variant.

The invention also includes transgenes comprising a DNA sequence encoding a lymphatic polypeptide variant.

Further, the invention includes a method for producing a transgenic non-human animal substantially depleted in a mature lymphocytic cell type. The method comprises introducing a transgene into an embryonal target cell. The transgene encodes a lymphatic polypeptide variant and is capable of inhibiting formation of a mature lymphocytic cell type. The thus transformed transgenic embryonal target cell is thereafter transplanted into a recipient female parent from which offspring having the desired phenotype are identified.

DETAILED DESCRIPTION OF THE DRAWINGS

FIG. 1A is a schematic representation of the αβ T cell receptor.

FIG. 1B depicts the αβ T cell receptor variant containing a deletion of the variable region of the β chain.

FIG. 2 depicts the genomic organization of the T cell receptor loci in mouse.

FIGS. 3A and 3B show the structure of the T cell receptor β transgene including nucleotide sequence of the variable region and restriction map of clone cos HY9-1.14-5.

Figure 5:
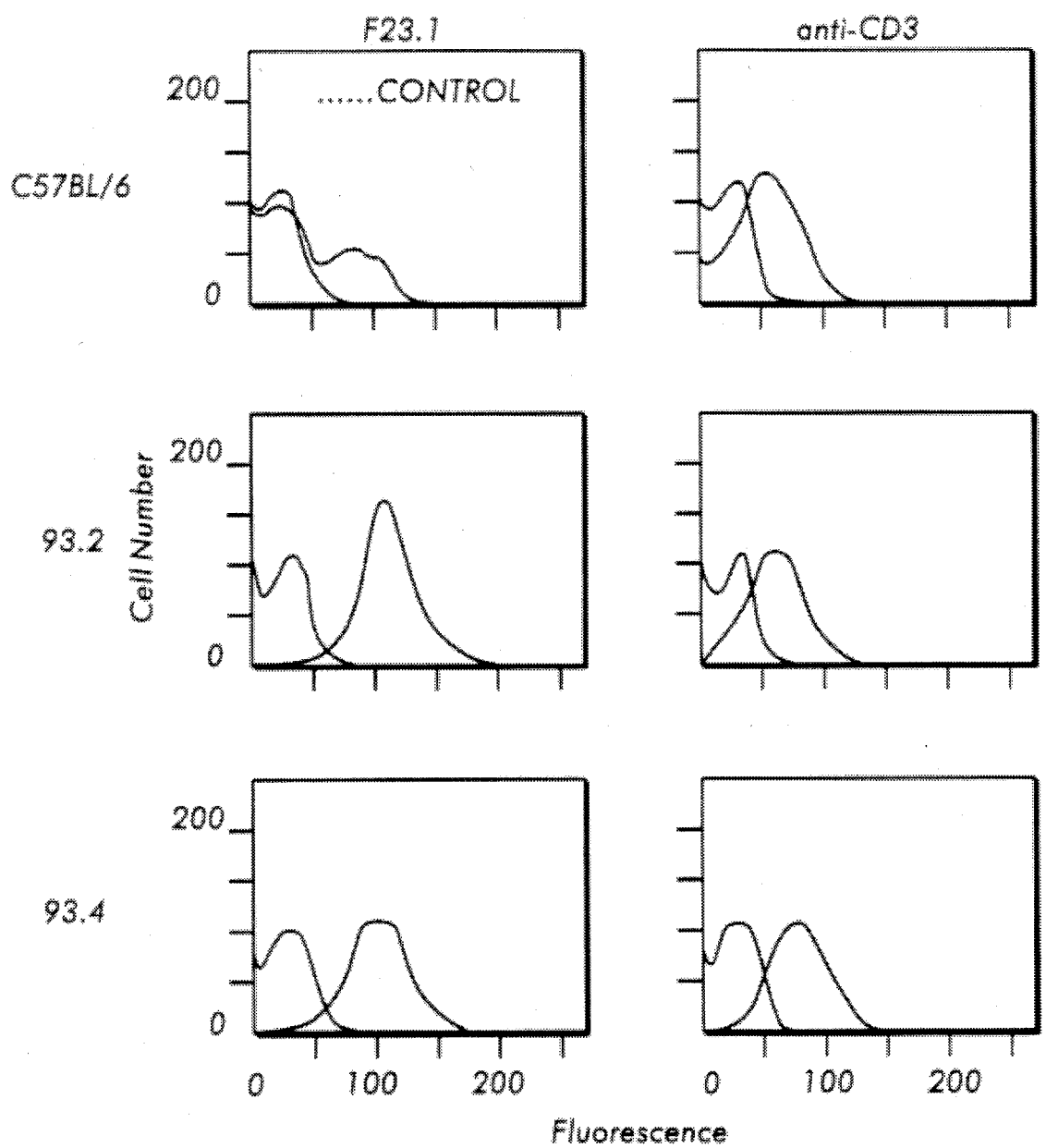

FIG. 5 demonstrates the surface expression of F23.1-positive β chains on T cells from transgenic and normal mice.

Figure 6A:
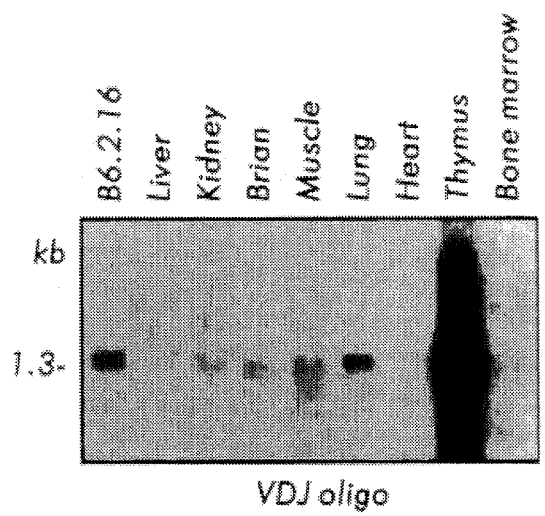
Figure 6B:
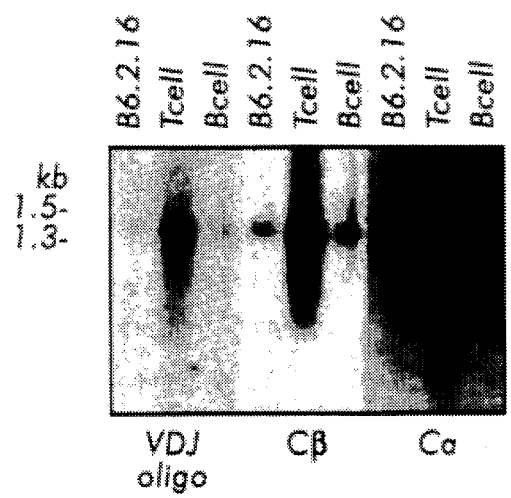

FIGS. 6A and 6B demonstrate the tissue specificity of transgene transcription.

Figure 7:
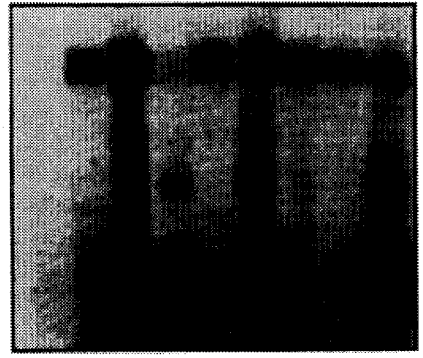

FIG. 7 is a gel electrophoretic analysis of immuno percipitated β chains from transgenic T lymphocytes before and after preclearing with F23.1 monoclonal antibodies.

Figure 8:
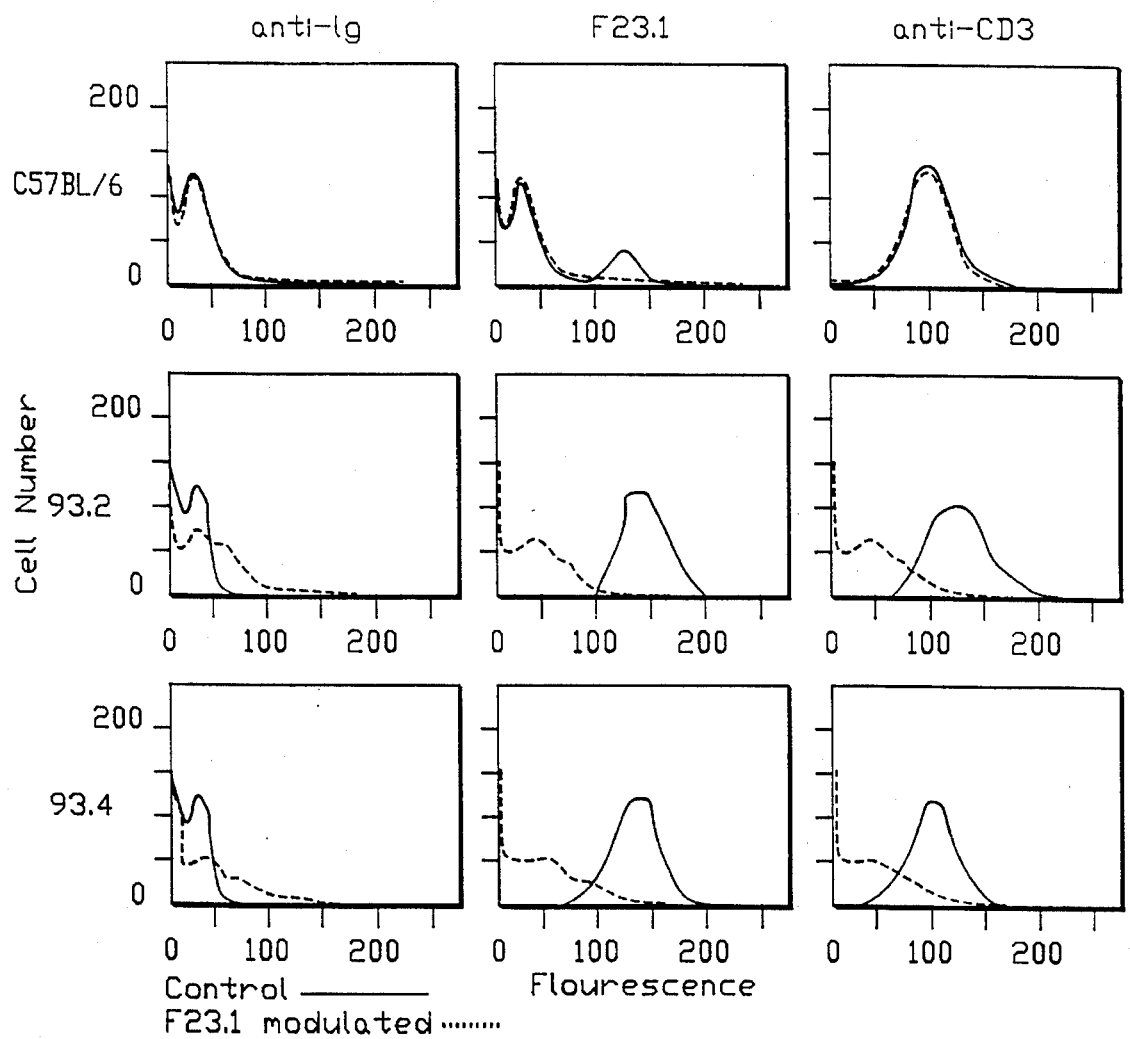

FIG. 8 demonstrates the modulation of surface expression of CD3 molecules on various T cells by Vβ8-specific F23.1 monoclonal antibodies.

Figure 9:
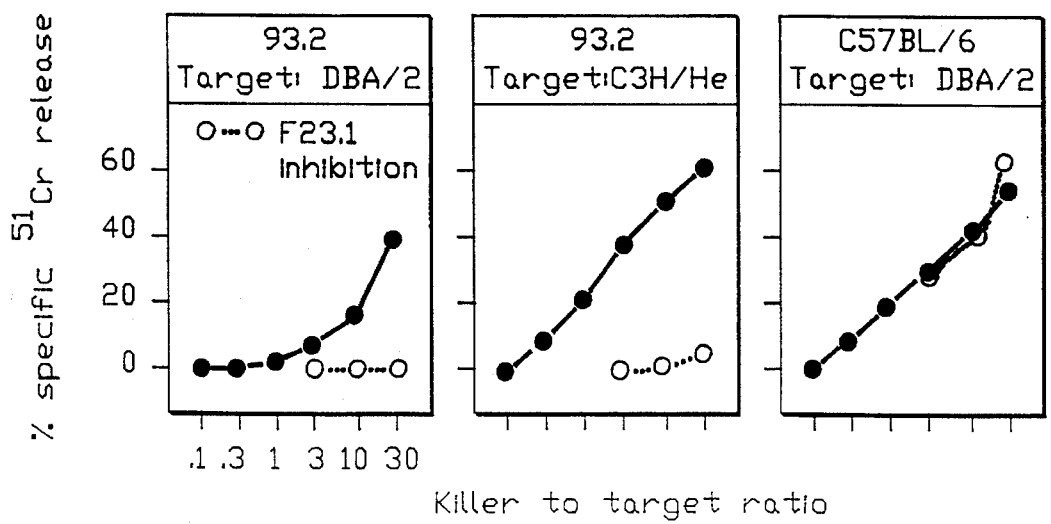

FIG. 9 demonstrates the inhibition of cytllytic activity of transgenic T cells by Vβ8-specific F23.1 monoclonal antibodies.

Figure 10C:
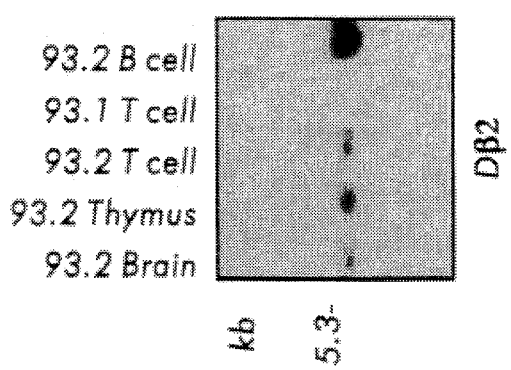
Figure 10B:
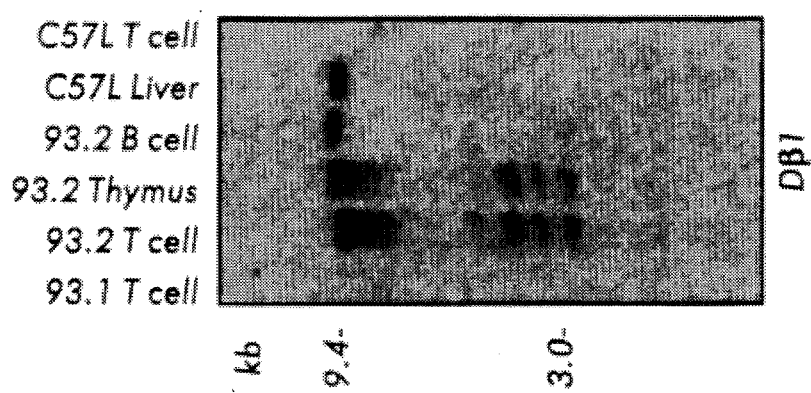
Figure 10A:
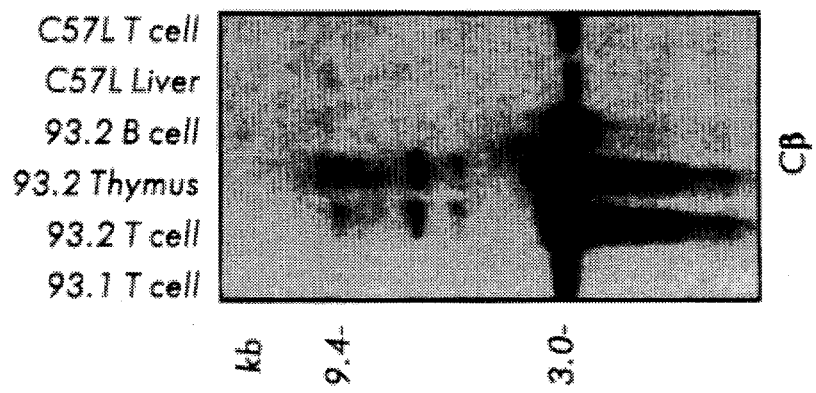

FIGS. 10A, 10B and 10C demonstrate that endogenous β genes in transgenic mouse 93.2 show predominantly partial Dβ1-Jβ rearrangements.

Figure 12:
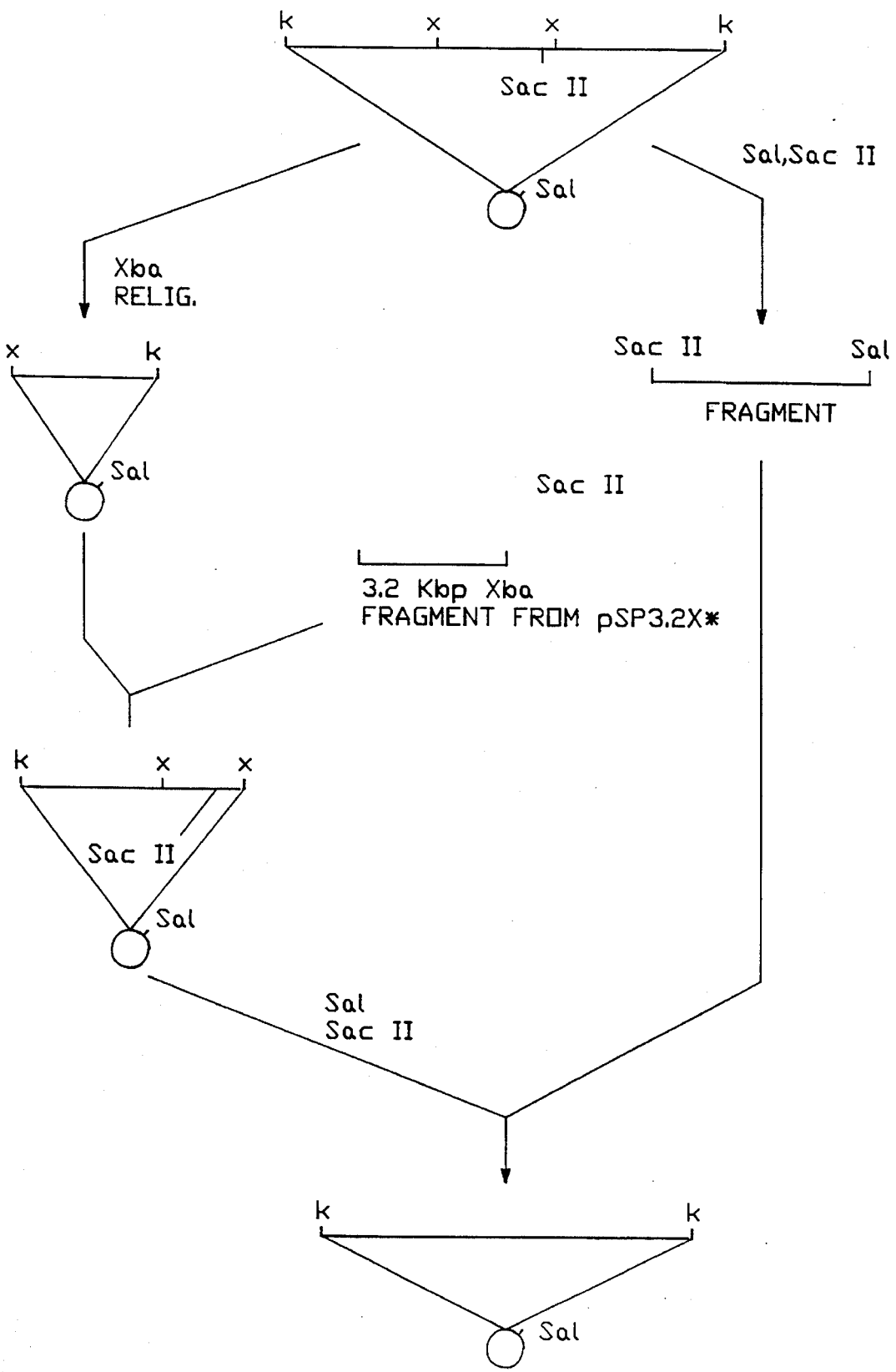

FIGS. 11A, 11B and 12 depict the construction of ΔV-TCRβ and ΔVs-TCRβ transgenes.

FIG. 13 demonstrates the expression of the ΔVs-TCRβ transgene.

Figure 14:
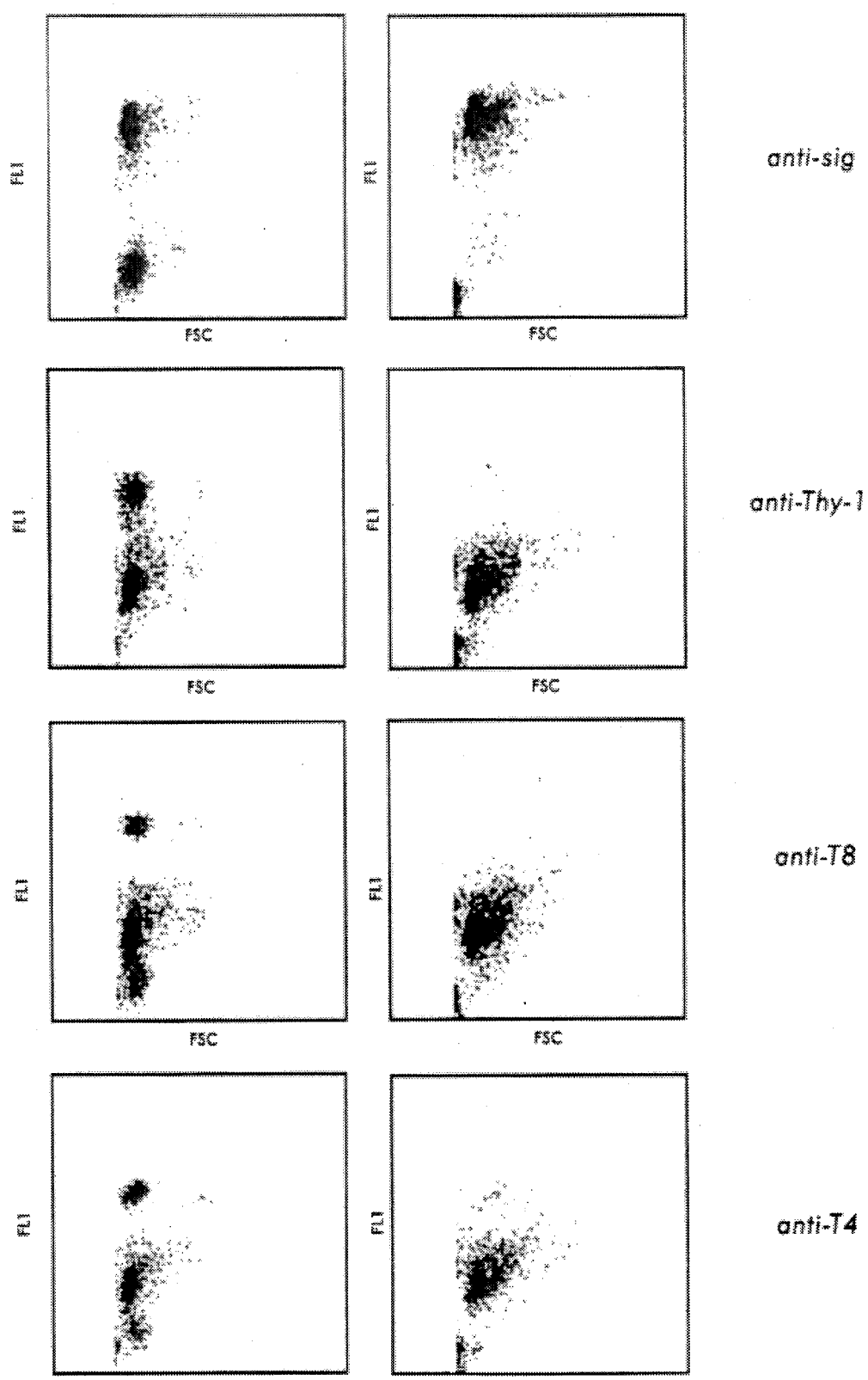

FIG. 14 is a surface marker staining profile of splenocytes from transgenic mouse #1670 and a control mouse.

FIGS. 15A, 15B and 15C depict the amino acid and known DNA sequence for transgenes TCRβ and ΔV-TCRβ based on partial CDNA and genomic sequence data.

DETAILED DESCRIPTION OF THE DISCLOSURE

The "non-human animals" of the invention comprise any non-human animal having an immune system capable of producing a humoral and/or cell-mediated immune response. Such non-human animals include vertebrates such as rodents, non-human primates, sheep, dog, cow, amphibians, reptiles, etc. Preferred non-human animals are selected from the rodent family including rat and mouse, most preferably mouse.

The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster, et al. (1985) *Proc. Natl. Acad. Sci. USA* 82, 4438–4442). As a consequence, all cells of the transgenic non-human animal will carry the incorporated transgene. This will in general also be reflected in the efficient transmission of the transgene to offspring of the founder since 50% of the germ cells will harbor the transgene. Micro-injection of zygotes is the preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *Proc. Natl. Acad. Sci USA* 73, 1260–1264). Efficient infection of the blastomeres is obtained by enzymatic treatment to remove the zona pellucida (Hogan, et al. (1986) in *Manipulating the Mouse Embryo,* Cold Spring Harbor Laboratory Press, Cold Spring Harbor, N.Y.). The viral vector system used to introduce the transgene is typically a replication-defective retrovirus carrying the transgene (Jahner, et al. (1985) *Proc. Natl. Acad. Sci. USA* 82, 6927–6931; Van der Putten, et al. (1985) *Proc. Natl. Acad. Sci USA* 82, 6148–6152). Transfection is easily and efficiently obtained by culturing the blastomeres on a monolayer of virus-producing cells (Van der Putten, Supra; Stewart, et al. (1987) *EMBO J.* 6, 383–388). Alternatively, infection can be performed at a later stage. Virus or virus-producing cells can be injected into the blastocoele (Jahner, D., et al. (1982) *Nature* 298, 623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the midgestation embryo (Jahner, D. et al. (1982) supra).

A third type of target cell for transgene introduction is the embryonal stem cell (ES). ES cells are obtained from pre-implantation embryos cultured in vitro and fused with embryos (Evans, M. J., et al. (1981) *Nature* 292, 154–156; Bradley, M. O., et al. (1984) *Nature* 309, 255–258; Gossler, et al. (1986) *Proc. Natl. Acad. Sci USA* 83, 9065–9069; and Robertson, et al. (1986) *Nature* 322, 445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240, 1468–1474.

As used herein, a "transgene" is a DNA sequence introduced into the germline of a non-human animal by way of human intervention such as by way of the above described methods. The transgenes of the invention include DNA sequences which are capable of suppressing cognate endogenous alleles. Further, such transgenes are capable of either facilitating or inhibiting the maturation of a lymphatic cell type. Such transgenes comprise DNA sequences encoding either a "lymphatic polypeptide" or "lymphatic polypeptide variant" which may be expressed in a transgenic non-human animal.

A lymphatic polypeptide corresponds to a naturally occurring polypeptide expressed selectively by lymphatic tissue and includes the wide variety of polypeptide chains associated with immunoglobulin production by plasma cells and TCRs produced by mature T cells. Such lymphatic polypeptides are produced by mature lymphocytic cell types after differentiation. Such differentiation involves the functional rearrangement of numerous gene regions and segments to form the DNA sequence encoding the naturally occurring lymphatic polypeptide (described in more detail hereinafter).

The term "cognate endogenous alleles" refers to alleles in the genome of the transgenic non-human animal which are closely related to the transgene introduced therein. Thus, for example, the alleles involved in TCRβ chain production in mouse T cells are cognate endogenous alleles which may be suppressed by a transgene comprising a DNA sequence encoding a TCRβ chain from mouse or other species. Further, such cognate endogenous alleles may include the γδ alleles involved in γδ TCR production.

The transgene encoding a lymphatic polypeptide, in addition to suppressing cognate endogenous alleles, is also capable of facilitating the maturation of the particular lymphocytic cell type which would normally express the cognate endogenous alleles if the lymphatic polypeptide is expressed. Thus, transgenic mice containing a transgene encoding a functionally rearranged βTCR chain contain mature T lymphocytes which express αβTCRs containing β chains encoded by the TCR β transgene.

Transgenes encoding lymphatic polypeptide variants, however, suppress cognate endogenous alleles and inhibit the maturation of the lymphocytic cell type which normally expresses such cognate endogenous alleles. The parameters which define the lymphatic polypeptide variant may be defined structurally and functionally.

As indicated in the Examples, a functionally rearranged mouse TCR fusion β gene which is expressed in a transgenic mouse, suppresses the expression of the cognate endogenous alleles encoding the β chain TCR gene. See also Uematsu, Y., et al. (1988) *Cell* 52, 831–841. The suppression of such expression apparently results from the blocking of the rearrangement process of the endogenous β genes during differentiation to the mature T lymphocyte. Partial D-J rearrangements are found in such transgenic animals while complete VDJ rearrangements are not detected. Such transgenic mice, however, do produce functional mature T cells. The αβ TCRs on such trangenic mice are homogeneous with respect to the β chain encoded by the transgene. They are, however, fully functional, at least in a variety of allogenic responses, presumably due to the diversity produced in such receptors by way of endogenous α chain rearrangements.

When, however, transgenic mice are produced containing a functionally rearranged TCR β gene which has had approximately 90% of the variable region deleted (ΔTCRβ), such mice failed to form a functional thymus and substantial T cell depletion was observed. Thus, disruption of the expression of functional TCRβ chains is sufficient to cause T cell depletion. The mechanism for this T cell depletion is not known. However, it is assumed that the TCR β gene encodes a lymphatic polypeptide having at least two functional domains related to the mechanism of T cell depletion when transgenes containing variable region deletions are used. One domain functions to suppress the expression of cognate endogenous alleles (such as the TCRβ chain alleles) presumably by a mechanism analogous to allelic exclusion observed during normal differentiation. The second functional domain is required for T cell maturation. In the case of the complete TCR β gene both functional domains are present in the trangenic TCR β chain as evidenced by the suppression of endogenous β alleles and the normal maturation of T lymphocytes. However, in the case of the transgene ΔV-TCRβ (containing a deletion of approximately 90% of the variable region), the transgenic ΔV-TCRβ polypeptide contains only a first functional domain capable of suppressing endogenous β chain alleles. A sufficient portion of the second functional domain is deleted such that T cell maturation is inhibited. See FIG. 1B.

Thus, structurally, the transgene, in one aspect of the invention, encodes a lymphatic polypeptide variant comprising a lymphatic polypeptide wherein all or part of the variable region is deleted. Preferably, at least part of the V segment of the V region is deleted. However, the deleted sequences may also include part of the D and/or J segment of the variable region of the lymphatic polypeptide.

The transgene encoding the lymphatic polypeptide variant also can be defined functionally. This definition is based on the two functional domains present in the naturally occurring lymphatic polypeptide. By analogy to the TCRβ chain, the first functional domain is capable of suppressing the expression of cognate endogenous alleles whereas the second functional domain is capable of inducing the maturation of a particular lymphocytic cell type. The lymphatic polypeptide variant contains the first functional domain but lacks the second. Although defined functionally, such domains can be structurally ascertained by way of the methodology disclosed in Examples 1 and 2 herein. For example, the first functional domain involved in the suppression of cognate endogenous alleles may be ascertained by generating a family of transgenes encoding specific deletions of portions of the lymphatic polypeptide. Transgenic mouse lines, containing each of these transgenes, for example, may then be analyzed to ascertain the suppression of endogenous alleles as described in Example 1. Those transgenes containing deletions which do not induce suppression of the endogenous alleles define the functional domain responsible for suppression of endogenous expression.

Once such structural domains are defined, the second functional domain may be defined structurally by generating a series of transgene constructs containing deletions of various portions of the lymphatic polypeptide not defining the first functional domain. Thus, sequential deletions (i.e., deletions of about 10–30 base pairs through, for example, the variable region) or progressive deletions (i.e., a set of deletions comprising deletion of approximately 10–20 base pairs to, for example, all of the DNA sequence encoding the variable region) can be used in conjunction with the methods of Example 2 to define the second functional domain required for lymphocyte maturation. Thus, lymphatic polypeptide variants and the transgenes encoding the same can be readily defined by such methods.

As indicated, the lymphatic polypeptide variant encoded by the transgene in one embodiment of the invention should be expressed in a precursor of the mature lymphocyte to be depleted in the transgenic animal. To be expressed, the transgene DNA sequence must contain regulatory sequences necessary for transcription of the transgene in the precursor cell type in the transgenic animal. Further, various regulatory sequences necessary for translation and if necessary processing of the mRNA transcripts encoded by the transgene are required. Such regulatory sequences include promoter sequences to control transcription, ribosome binding sites to facilitate translation, splice acceptor and splice donor sequences for intron excision, polyadenylation sequences, transcription and translational termination signal and enhancer sequences which facilitate the efficient expression of the lymphatic polypeptide variant. In most cases, a secretory signal sequence will also be included to facilitate the association of the lymphatic polypeptide variant with the membrane of the cell expresssing the transgenic polypeptide. Transgenes therefore encode all of the regulatory sequences necessary to express the lymphatic polypeptide or lymphatic polypeptide variant encoded by the transgene. Of course, each of the regulatory sequences and encoding sequences are operably linked to produce a functional transgene capable of expressing the trangenic polypeptides in the non-human transgenic animal.

"Operably linked" when describing the relationship between two DNA or polypeptide sequences simply means that they are functionally related to each other. For example, a signal or leader sequence is operably linked to a peptide if it functions as a signal sequence participating in the insertion of the immature form of the protein into a cell membrane. Similarly, a promoter is operably linked to a coding sequence if it controls the transcription of the sequence; a ribosome binding site as operably linked to a coding sequence if it is positioned so as to permit translation, etc.

Transgenes are derived, for example, from DNA sequences encoding at least one polypeptide chain of a T cell receptor (TCR) or one polypeptide chain of the immunoglobulin (Ig) molecule. Preferably, a modified form of the β or γ chain of the TCR and most preferably the β chain of the TCR is used as a transgene to inhibit the formation of mature T cells. In the case of B cells, a derivative of the heavy chain of the Ig molecule is preferred to inhibit the formation of antibody producing plasma cells derived from B cells. Generally, such transgenes are derived by deleting from the DNA sequence encoding a functionally rearranged β chain, γ chain or heavy chain polypeptide, all or part of the DNA sequence encoding the variable region of such molecules. Preferably all of the variable region is deleted although small segments of 5' sequences encoding an N-terminal portion of the V segment and 3' sequences encoding the C-terminal portion of the J segment may be retained in the transgene. At the very least, all or part of the variable segment should be deleted. Thus, transgenes generally comprise C regions of the β chain, γ chain or heavy chain polypeptides of TCR and Ig molecules respectively but may also include additional sequences encoding all or part of the J and D segments of the variable region.

Transgenic mice containing a transgene encoding a TCRβ chain having its variable regions deleted do not contain detectable T cells. Further, transgenic mice containing immunoglobulin heavy chain wherein all or part of the variable region is deleted are expected to be incapable of producing plasma cells which secrete immunoglobulins. This is because during B cell development, B cells rearrange their Ig heavy chain genes first. Once a functionally rearranged Ig heavy chain gene is generated, light chain rearrangement starts. This eventually will result in the production of complete IgM molecules containing two heavy and two light chains. Such IgMs are not secreted since their C regions contain a membrane anchoring domain. During further develoment, the B cells switch the use of the constant region to other constant regions that do not encode a transmembrane domain, e.g., IgG. When this switch occurs, they become plasma cells which secrete large amounts of specific immunoglobulin. In order to develop into plasma cells, the IgM producing B cells must interact with other cells of the immune system via the IgM located on the B cell surface. Since the heavy chain of the IgM variant contains the deletion of all or part of the variable region, transgenic non-human animals containing a transgene encoding such a deleted heavy chain should not be able toproduce B cells which can interact with the immune system to form the mature plasma cell type.

Alternatively, the transgene may comprise a DNA sequence encoding a lymphatic polypeptide variant which is incapable of being expressed in the precursor stem cell or latter precursor of the lymphocytic cell type to be depleted. Such DNA sequences may contain one or more mutations involving the insertion or deletion of one or more nucleotides that may, for example, result in a frame shift or nonsense mutation (e.g., stop codon) that prevents all or part of the expression of the transgene. The transgene, however, has sufficient sequence homology with a cognate endogenous allele such that when introduced into an ES target cell it may homologously recombine with such an allele in the ES cell to disrupt its expression. See, e.g., Kirk and Capecchi (1978) Cell 51, 503–512. After identification and selection of ES cells containing the transgene in the targeted allele, a transgenic non-human animal may be produced by colonizing an appropriate embryo with the selected ES cell.

In the case of T cells, the Cβ1 and Cβ2 alleles for the TCRβ chain and most preferably the Cα allele for the TCRα chain are targeted for insertion of a transgene which disrupts expression of the allele. For example, in the case of the Cα allele, once a genotype is identified containing a transgene disrupting Cα expression, cross-breeding can be used to produce transgenic animals homozygous for the Cα⁻ genotype. Such homozygotes should also be deficient in mature T cells since they are incapable of producing the functional αβTCR required for T cell maturation.

A similar approach can be used to produce plasma cell deficient transgenic animals. In that case the transgene is targeted to disrupt the expression of Cμ and Cδ portions of the IG heavy chain.

Transgenic non-human animals depleted in one or more mature lymphocytic cell types, such as transgenic mice depleted in mature T cells or plasma cells, have multiple uses. For example, T cell depleted mice do not have a cell-mediated immune response. They are therefore suitable for testing drugs that interfere with cell-mediated immunity for side effects and complications, e.g., kidney damage, etc. Thus, antibiotics, anti-vital drugs, antifungal agents and immunosuppressive drugs such as cyclosporine may be administered to such mice to ascertain their effects.

In addition, such T cell deficient mice do not have T4 (helper) cells used in the B cell humoral response. They can, therefore, be used for testing the effects of passive immunization. Further, the lack of a cell-mediated immune response renders such transgenic mice prone to develop tumors since they are not protected by immuno-surveillance. They therefore can be used to test the carcinogenicity of various materials. In addition, materials may be tested in such animals which may confer protection against the development of neoplasms.

Further, such T cell depleted mice can be used as model systems for AIDS and SCID involving the depletion of T cells.

Plasma cell deficient transgenic mice, in combination with T cell depleted mice, offer a good model system to study the effect of the depletion of the humoral immune response, cell-mediated immune response or both. Further, such plasma cell depleted and/or T cell depleted mice can be used as a model system to study SCID syndromes involving the depletion of B, T and/or B and T cell types.

The genes encoding the various segments and regions which may be used in the invention are well characterized.

The TCRs associated with T cells represent an enormous percent of clonally varying molecules with the same basic structure. The TCR is a heterodimer of 90 kd consisting of two transmembrane polypeptides of 45 kd each connected by disulfide bridges (FIG. 1A) (Samuelson, et al. (1983) *Proc. Natl. Acad. Sci. USA* 80, 6972; Acuto, et al. (1983) *Cell* 34, 717; MacIntyre, et al. (1983) *Cell* 34, 737). For most T cells, the two polypeptides are referred to as the α and β chain. Like the heavy and light chains of the immunoglobulins, the α and β chains have variable (V) and constant (C) regions (Acuto, et al. (1983) supra; Kappler, et al. (1983) *Cell* 35, 295). The V region is responsible for antigen recognition and the C region is involved in membrane anchoring and signal transmission. A small percentage of lymphoid T cells, however, have a different set of TCRs comprising different polypeptide chains referred to as γ and δ chains (Borst, et al. (1987) *Nature* 325, 683; Brenner, et al. (1987) *Nature* 325, 689; Bank, et al. (1986) *Nature* 322, 179; Pardoll, et al. (1987) *Nature* 326, 79).

Using subtractive hybridization procedures, cDNA clones encoding the TCR polypeptide chains have been isolated (Mendrick, et al. (1984) *Nature* 308, 149; Hendrick, et al. (1984) *Nature* 308, 153; Yanagi, et al. (1984) *Nature* 308, 145; Saito, et al. (1987) *Nature* 325, 125; Chien, et al. (1984) *Nature* 312, 314). Sequence analysis of these cDNA clones reveal the complete primary sequence of the TCR polypeptides. The TCR polypeptides are all similar to each other and to the immunoglobulin polypeptides. For review see Davis and Bjorkman (1988) supra.; and Kronenberg, et al. (1986) *Ann. Rev. Immunol.* 4, 529). The variable region of the TCR chains is composed of a variable region (V) and a constant region (C). The variable region of the TCR chains is further subdivided into a variable (V) and joining (J) segments. In addition, the variable region of the α and β chains also contains a diversity (D) segment interposed between the V and J segments. At similar positions as in the immunoglobulins, hypervariable regions are present in the variable region of the TCR. Two hypervariable regions are encoded in the V region whereas one is represented by the junction between the V and J or V, D and J segments. The constant region of the TCR chains is composed of four functional regions often encoded by different exons (Davis and Bjorkoran (1988) supra.). The TCR C regions show typical immunoglobulin-like characteristics such as the presence of cystine residues involved in the linking of two β sheets which probably fold into immunoglobulin-like domains. All TCR chains have a hydrophobic transmembrane region in which a highly conserved lysine residue is present.

The availability of TCR cDNAs permits an analysis of the genomic organization of the murine and human TCR genes. The TCR genes show a segmental organization similar to the immunoglobulin genes. FIG. 2 shows a schematic representation of the four TCR gene loci. In the β chain gene locus, two nearly identical Cβ regions are tandemly arranged, each preceded by one D and six J segments (Kronenberg, et al. (1986), supra; Davis, M. (1985) *Rev. Immunol.* 3, 537). The β locus also contains approximately 20 to 30 V segments (Barth, et al. (1985) *Nature* 316, 517; Behlkey, et al. (1985) *Science* 229, 566), one of which is located 3' to the C regions in opposite orientation (Malissen, et al. (1986) *Nature* 319, 28). The γ locus is less diverse, containing three Jγ-Cγ regions and only a limited number of V segments (Hayday, et al. (1985) *Cell* 40, 259; Chien, et al. (1987) *Nature* 330, 722). The α and δ loci overlap each other in that many of the δ coding segments are located within the segments of the α gene (Chien, et al., supra; Elliott, et al. (1988) *Nature*, 331, 627). As a consequence, the δ segments are deleted in most αβ bearing T cells (Lindsten, et al. (1987) *J. Exp. Med.* 166, 761). Thus, the α and γ chain genes are encoded by variable and joining segment and constant regions whereas the β and δ chain genes contain variable, diversity and joining segment and a constant region. During somantic development of the T cell, a functional TCR gene is formed by rearrangement of these segments and regions. This process is the basis for T cell receptor diversity. The following strategies have been postulated for T cell diversification: (1) multiple germline V and J segments (Kronenberg, et al. (1986) supra; (2) D segments that can be translated in all three reading frames in the case of β and γ genes (Goverman, et al. (1985) *Cell* 40, 859; Elliott, et al. (1988), *Nature* 331, 627); (3) combinatorial joining of V, D and J segments; (4) the random addition of nucleotides between the V, D and J segments (N-region addition) (Davis and Bjorkman (1988) supra); (5) the flexibility of several V segments with respect to the position of their 3' joining points (Davis and Bjorkman, supra); and (6) the combinatorial joining of TCR chains.

As shown schematically in FIG. 2, the encoding segments for the TCR genes are scattered over large arrays of chromosomal DNA. Like the immunoglobulin genes, specific V, D and J segments are fused together to generate a complete V coding region next to a C region. In B and T cells, the rearrangements are mediated by similar sequences flanking the segments to be fused (Akira (1987) *Science* 238, 1134; Yancopoulos, et al. (1986) supra.). These sequences consist of conserved heptamer and monomer stretches spaced by 12 or 23 nucleotides. Depending on the orientation of the segments being joining, looping out/deletion or inversion of large genomic DNA can occur (Fujomoto (1987) *Nature* 327, 242; Okazaki, et al. (1987) *Cell* 49, 477; Mallisen, B., et al. (1986) supra). B and T cells probably use the same machinery for the assembly of Ig and TCR since B cells rearrange transfected TCR segments in the same way as transfected Ig gene segments (Yancopoulos, et al. (1986) supra). The TCR β, γ and δ genes are rearranged and transcribed first, followed by the TCR α gene (Chien, et al. (1987) supra; Pardoll, et al. (1987) *Nature* 326, 79; Raulet, et al. (1985) *Nature* 312, 36; Samelson, et al. (1985) *Nature* 315, 765; Snodgrass, et al. (1985) *Nature* 315, 232).

The regulation of immunoglobulin gene assembly and expression is intrinsicly related to the progression of B-cell precursors to the B cell differentiation stage. For a review of the mechanism of Ig variable region gene assembly and regulatory mechanisms to control genomic rearrangements, see Yancopoulos, et al. (1986) supra. Ig gene assembly in B cells closely parallels that for TCR assembly in T cells. In addition, a number of transgenic mice containing a number of immunoglobulin genes have been prepared to further study the mechanism of Ig expression, allelic exclusion and rearrangement mechanisms (Storb (1987) *Ann. Rev. Immunol.* 5, 151–174).

Thus, the αβ and γδ TCRs of T cells and the heavy and light chains of Ig molecules in B cells have been well characterized. As indicated, the transgenes of the present invention are derived form such DNA sequences, preferably those encoding the β and γ chains of the T cell receptors, most preferably the β chain, and the heavy (H) chain of the Ig molecule from B cells. Such DNA may be obtained from the genome of somatic cells and cloned by well established technology. Such cloned DNA sequences may thereafter be further manipulated by recombinant techniques to construct the transgenes of the present invention. However, a more efficient and preferred methodology is to clone a functionally rearranged β or γ TCR gene or a functionally rearranged heavy Ig gene. Such cloned functionally rearranged genes generally will have all necessary regulatory and secretory sequences for expression of the functionally rearranged gene in the B or T lymphocytes of the animal from which the sequence is derived, including introns which are necessary for the efficient expression of transgenes (Brinster, et al. (1988) *Proc. Natl. Acad. Sci. USA* 85, 836). Such DNA sequences can be derived by generating cultures of T or B cells from mature animals or animals which have been challenged with an antigen. The DNA from one or more such clones may be used to generate a genomic DNA library in hosts such as λgt11 and EMBL 3 following published procedures (Young, R. A., et al. (1983) *Proc. Natl. Acad. Sci. USA* 80, 1194–1198; Frischauf, et al. (1983) *J. Mol. Biol.* 170, 827–842). Such libraries may then be screened with appropriate probes to particular regions or segments of the β and/or γ genes for TCRs or the heavy gene for Ig molecules depending on the source of the genomic DNA. Such probes preferable are specific for a part of one of the C regions of the molecule of interest. cDNA clones from the same cellular clone may also be generated and identified by similar probes. The sequences of such cDNA clones facilitates the identification of the coding sequence of the genomic clone thereby permitting the identification of putative introns and regulatory sequences.

If a particular genomic clone does not contain the entire coding region for the functionally rearranged chain or if it does not contain regulatory or enhancer regions typically located in 5' or 3' flanking regions, that DNA sequence may be recombined with other clones to provide such sequences. Thus, for example, a genomic clone from the T cell clone B6.2.16 (described in more detail in the Examples) has flanking sequences comprising 2 kb 5' and 2 kb 3' from the coding region for the mouse TCR β gene. This DNA sequence is inactive in transgenic mice because it lacks a 550 base pair enhancer sequence located 5 kb downstream from the Cβ2 locus (Krimpenfort, P., et al. (1988) *EMBO J.* 7, 745–750). A fusion construct was therefore prepared containing a larger extension of the 3' end. A cosmid clone derived from BALB7c liver DNA containing the Cβ2 and downstream region was used to generate this fusion construct which is active in transgenic mice (Krimpenfort, P., et al. (1988) supra). Similar methods may be used to generate fusion genes containing all the necessary DNA sequences for regulation of the expression of the DNA sequences encoding the particular polypeptide chain of interest.

The DNA sequences from which the transgene is derived are preferably obtained from the functionally rearranged genome of the same species of animal into which the transgene will be introduced. Thus, functionally rearranged β and γ genes from mouse TCR are preferred for making transgenes for use in transgenic mice. The invention, however, is not limited to transgenes derived from the same species of animal used to form transgenic non-human animals. It has recently been shown that two independent lines of transgenic mice containing either the human heavy chain of HLA class I antigen or the light ($\beta_2$-microglobulin) chain of human HLA class I antigen can be crossed to produce a functional HLA class I antigen which is biochemically indistinguishable from the same antigen expressed on human cells (Krimpenfort, P., et al. (1987) *EMBO J.* 6, 1673–1676. Other examples of heterologous transgenic expression include the heterologous regulatory and structural sequences disclosed in EPO Publication No. 0247494 and PCT Publication No. WO88/00239. Thus, DNA sequences from species different from that of the transgenic animal ("heterologous DNA") may be used to form the transgenic non-human animals of the present invention. Such heterologous sequences include regulatory and secretory sequences as well as structural DNA sequences which when modified encode heterologous lymphatic polypeptide variants capable of inhibiting the formation of a mature lymphocytic cell type. The only limitation on the use of such heterologous sequences is functional. The heterologous regulatory sequences must be utilized by the transgenic animal to efficiently express sufficient amounts of the lymphatic polypeptide variant such that it is able to inhibit the formation of a mature lymphocytic cell type. Further, the heterologous lymphatic polypeptide variant when properly expressed in the transgenic animal must be capable of producing the desired depletion of a lymphocytic cell type. Thus, by analogy to expression of human HLA antigens on the cell surface of transgenic mice, a functionally rearranged human TCRβ gene containing a variable region deletion can be used to express a human β TCR variant capable of suppressing the formation of mature T cells in transgenic mice. Further, it should be posible to mix homologous and heterologous DNA sequences (e.g., homologous regulators with heterologous structural genes and vice versa) to produce functional transgenes which may be used to practice the invention. Alternatively, heterologous DNA sequences encoding lymphatic polypeptide variant must be capable of inhibiting the expression of functional lymphatic polypeptide required for the maturation of a lymphocytic cell type by disrupting the expression of cognate endogenous alleles.

The following is presented by way of example and is not to be construed as a limitation on the scope of the invention. Further, all references referred to herein are expressly incorporated by reference.

EXAMPLE 1

Suppression of Cognate Endogenous Alleles of TCRβ

This example describes the construction of a transgene which when expressed is capable of suppressing the expression of cognate endogenous alleles for the TCRβ chain. When introduced into a mouse, the transgenic mouse so produced expresses TCR receptors substantially containing only the TCRβ chain encoded by the transgene.

Establishment of the Male-Specific B6.2.16 Clone

C57BL/6 female mice were immunized with $10^7$ male spleen cells injected intraperitoneally. After days, $2 \times 10^7$ female spleen cells were cultured with $2 \times 10^7$ x-irradiated male cells in 8 ml of culture media. After 12 days, $10^6$ viable female responder cells were restimulated with $10^7$ x-irradiated male cells in 1 ml of medium containing interleukin-2 (IL-2). Cells were cloned by culturing 0.3 cells with stimulators as described below. Clones were tested for cytolytic activity as described below, and clone B6.2.16 was selected after surface staining of various clones with the F23.1 antibody (von Boehmer and Haas, (1986) *Meth. Enzymol.* 132, 467–477; Staer, et al. (1985) *J. Immunol.* 134, 3994–4000) which binds to all three members of the Vβ8 family (Behlke, et al. (1982) *J. Exp. Med.* 165, 257–267).

Isolation and Characterization of β Chain cDNA and Genomic Clones

Total RNA and high molecular weight DNA were isolated from cytotoxic T cell clone B6.2.16 and used to construct cDNA and genomic DNA libraries in λgt11 and EMBL3, respectively, following published procedures (Young and Davis (1983) *Proc. Natl. Acad. Sci. USA* 80, 1194–1198; Frischauf, et al. (1983) *J. Mol. Biol.* 170, 827–842). Both libraries were screened with a Cβ probe corresponding to the sequence of the Cβ2 region reported by Mallisen, et al. (1984) *Cell* 37, 1101. Positive clones were characterized by mapping with restriction endonucleases and hybridization with probes specific for the Dβ1 gene segment, 1 1.4 kp Pst1 fragment entending 1.25 kb 5' to the Dβ1 gene segment (Siu, et al. (1984) *Nature* 311, 344–350), and Jβ gene segment. A full-length cDNA clone and genomic clones, λ8 for the functional allele and λ3 for the nonfunctional allele, were subcloned into M13mp18 for DNA sequence determination. Sequencing primers were the 17-mer universal M13 primer (Amersham) and 15- to 17-mer oligonucleotides synthesized to extend DNA sequence information beyond what was determined with M13 primers.

DNA sequence determination of the cDNA clone (FIG. 3A) showed that it was derived from a functionally rearranged β gene composed of the Vβ5.1 leader, Vβ8.2; a short portion of the Dβ2 segment, Jβ2.3; and the Cβ2 gene segment. One of the two β alleles, isolated in clones λ8 by restriction mapping and DNA sequencing showed that it contains the rearranged vβ8.2 gene about 100 bp downstream of an apparently inactive Vβ8.2 leader exon, while the Vβ5.1 leader sequence is located about 2.5 kb farther upstream (FIG. 3B). Splicing of the Vβ5.1 leader exon to the Vβ8.2 exon in T cells derived from C57BL/6 mice has been described by Chou, et al. (1987) *Proc. Natl. Acad. Sci. USA* 84, 1992–1996. The second α allele in B6.2.16 contains an incomplete Dβ1-Jβ2.5 rearrangement (not shown).

For the production of transgenic mice, a functionally rearranged β gene with long 5' and 3' flanking sequences was used. This was because initial experiments with clone λ8 containing only 1.2 kb of 5' and 3 kb of 3' flanking sequence failed to give expression in nine independently obtained transgenic mice.

Transgene Reconstitution

From the genomic clone λ9, a 13 kb SalII-SacII fragment, containing the functionally rearranged Vβ gene with 9 kb of 5' flanking sequence, was fused by way of a unique Sac II site to a 23 kb Sac II-Sal I fragment containing Jβ2 and Cβ2 gene segments together with 18 kb of 3' flanking sequence. The latter fragment was isolated from cosmid clone cos H-2$^d$II-1.14T derived from a BALB/c liver library, previously described (Steinmetz, et al. (1986) *Cell* 44, 895–904). See FIG. 3. Both fragments were ligated in the presence of Sal I-digested pTCF cosmid vector DNA arms. Ligation was checked by agarose gel electrophoresis. In vitro packaging and transformation of *E. coli* strain 490A was carried out as previously described (Steinmetz, et al. (1985) *Methods in Molecular Immunology in Immunological Methods*, Vol. III, Letkovits and Pernis, eds. (Orlando, Fla., Academic Press)). Several clones were picked and clone cos HYβ9-1.14-5, containing the reconstituted transgene as shown in FIG. 3B, was identified by restriction endonuclease mapping.

Transgenic Mice

The 36 kb insert of cos HYβ9-1.14-5 was released by SalI digestion and isolated by preparative agarose gel electrophoresis and electroelution. The DNA was extracted twice with phenol-chloroform and precipitated with ethanol. The DNA pellet was dissolved in ultrapure water and dialyzed against 10 mM Tris-HCl, 0.1 mM EDTA (pH 7.4). The DNA was adjusted to a final concentration of 4 μg/ml. Fertilized mouse eggs were recovered in cumulus from the oviducts of superovulated (CBA/BrA×C57BL/LiA)F$_1$ females that had mated with F1 males several hours earlier. Strains CBA/BrA and C57BL/L.A were obtained from The Netherlands Cancer Institute breeding facility, Amsterdam. Approximately 100 copies of the β gene were injected in the most accessible pronucleus of each fertilized egg, as described by Hogan, et al. (1986) *Manipulating the Mouse Embryo* (Cold Spring Harbor, N.Y., Cold Spring Harbor Laboratory Press. Microinjected eggs were implanted into the oviducts of one-day pseudopregnant (CBA/BrA×C57BL/LiA)F$_1$ foster mothers and carried to term. Several weeks after birth, total genomic DNA was isolated from tail biopsies of the pups. Mice that had incorporated the injected DNA in their genome were used for further breeding.

Southern and Northern Blot Analyses

Tail DNA was purified from the terminal quarter of tails of 4-week-old mice. The skin was separated from the bone and homogenized in 1 ml of 1% NaCl, 10 mM EDTA (pH 8.0), on ice by using a Polytron with a PTA7 blade. DNA was isolated by phenol-chloroform extraction and dialyzed against 10 mM Tris, 1 mM EDTA (pH 8.0) (TE). One milliliter of 6% p-aminosalicylate was added to the first phenol extraction. Mouse organs were chopped in ice-cold PBS and homogenized in 4M guanidinium isothiocyanate. 0.5 mM sodium citrate (pH 7.0), 0.1M β-mercaptoethanol, 0.5% Sarkosyl, using a Polytron as above. From the homogenate, RNA and DNA were isolated by differential centrifugation as described previously (Maniatis, et al. (1982) *Molecular Cloning: A Laboratory Manual* (Cold Spring Harbor, N.Y., Cold Spring Harbor Laboratory Press). DNA-containing fractions were dialyzed against TE buffer for 6 hr. extracted with phenol-chloroform three times, and dialyzed against TE overnight.

Total cellular RNA (5 to 10 μg) was separated on 1.5% formaldehyde-agarose gels according to Rave, et al. (1979) *Bucl. Acad. Res.* 6, 3559–3527) and transferred to Zeta probe membranes (BioRad) or BA85 nitrocellulose filters (Schleicher & Schull). Genomic DNAs (10 μg) were digested to completion with restriction endonuclease, separated on 0.6% agarose gels, and transferred to Zeta probe membranes according to Reed and Mann (1985) *Nucl. Acad Res.* 13, 7201–7221.

Northern blot hybridization with labeled restriction fragments was performed by using the same conditions as for Southern blot hybridization described by Steinmetz (1986), supra. Hybridization with the 30-mer oligonucleotide containing the VDJ joining region of the transgene was done in 900 mM NaCl, 90 mM Tris-HCl (pH 7.2), 6 mM EDTA, 10× Denhardt's solution, 1% SDS, and 500 μg/ml *E. coli* DNA at 42° C. overnight. After hybridization the filter was washed twice in 6× SSC, 0.1% SDS, at room temperature and twice in 3× SSC, 0.1% SDS, at 60° C. for 10 min. each. Southern blot hybridization was carried out as described by Uematsu, et al. (1988) *Immunogenetics* 27, 96–101. Filters were exposed with Kodak X-Omat S or X-Omat AR films at −70° C. for 2 hr. to 1 month using intensifying screens.

For hybridization we used previously described Cα and Cβ probes were used (Dembic, et al. (1985) *Nature* 314, 271–273; Snodgrass, et al. (1985) *Nature* 313, 592–595. The Jβ2 probe is a 1.2 kb ClaI-EcoRI fragment located immediately downstream of the Jβ2 gene segments (Chien, et al. (1984) *Nature* 309, 322–326). The Dβ1 probe is a 1.4 kb upstream of the Dβ2 gene segment, (Siu, et al. (1984) supra. The Cβ1-specific probe was derived from the 3' untranslated region as described by Gascoigne, et al. (1984) *Nature* 310, 387–391. The transgene-specific VDJ probe is an oligonucleotide of 30 residues in length identical to the complementary strand of the underlined cDNA sequence shown in FIG. 3A from position 581 to 610. Vβ7, Vβ9, Vβ11, Vβ12, Vβ14, Vβ15 and Vβ16 probes have been described by Lai, et al. (1987) *Proc. Natl. Acad. Sci. USA* 81, 3846–3850.

Surface Staining of Lymphocytes

Single-cell suspensions were prepared from lymph node or spleen. Cells were incubated with various monoclonal antibodies purified from supernatants of antibody-producing hybridoma cells. Cells (106) were incubated with a saturating dose of antibody at 0° C. for 20 min, washed, and incubated again with fluorescein isothiocyanate (FITC) coupled goat anti-mouse immunoglobulin antibodies. In some experiments, antibodies coupled with biotin were used in the first step followed by incubation with FITC-avidine (Kisielow, et al. (1984) *J. Immunol.* 133, 1117–1123).

Modulation and Immunoprecipitation of Surface Antigens

For modulation, cells were incubated with an excess of F23.1 antibodies (50 µg/ml) and rabbit anti-mouse immunoglobulin antibodies for 24 hr. at 37° C. Viable cells were obtained by spinning the suspension through Ficoll. For immunoprecipitation, $10^7$ B6.2.16 cloned T cells, C57BL/6 T cells, and 93.2 T cells were labeled with 0.5 mCi of NaI (Amersham) by the lactoperoxidase/glucoseoxidase method (Goding (1980) *J. Immunol.* 124, 2082–2088) for 20 min. at room temperature in PBS. The cells were washed five times with ice-cold PBS containing 0.1% $NaN_3$ and 17 mg/ml KCl and were then lysed for 30 min. on ice with a buffer containing 2% Triton X-100, 20 mM Tris (pH 8), 150 mM NaCl, 3 mM $MgCl$, 0.1 mM PMSF, and 5 mM iodoacetamide. The lysate was centrifuged for 5 min. in an Eppendorf centrifuge. Half of each sample was precleared four times with 100 µl of F23.1 antibodies coupled to Sepharose beads. Precleared and untreated lysates were then incubated with 5 µg of an anti-β panspecific antibody (Traunecker, et al. (1986) *Eur. J. Immunol.* 16, 851–854) for 2 hr. on ice, and subsequently incubated with 35 µl of 50% protein A beads. All samples were washed with high sale (lysis buffer containing 1 mg/ml ovalbumin and 0.65M NaCl) and low salt (lysis buffer containing 0.15M NaCl) buffers. Samples were reduced with 2-mercaptoethanol and analyzed on a 12.5% polyacrylamide gel. Autoradiography was accomplished with Kodak X-Omat AR film and intensifying screens.

Generation of Cytolytic T cells and Cytolytic Assay

Spleen ($10^7$) or lymph node ($10^7$) cells were cultured with $10^7$ x-irradiated (2000 rads) allogeneic stimulator cells for 5 days in 4ml of culture medium. $^{51}$Cr-labeled target cells were prepared by stimulating spleen cells from various mouse strains with concanavalin A (Con A) (2.5 µg/ml) for 48 hr. at $10^6$ cells per ml. Con A blasts were purified by centrifugation over Ficoll, and viable cells were $^{51}$Cr-labeled by incubation in $^{51}$Cr for 1 hr. at 37° C. In the cytolytic assay, $10^4$ $^{51}$Cr-labeled targets were incubated with various numbers of cytolytic T cells for 3.5 hr. at 37° C. in serial bottom wells in 200 µl of medium. The plates were centrifuged and 100 ml of supernatant removed to determine released $^{51}$Cr (Pohlit, et al. (1979) *Eur. J. Immunol.*, 9, 681–690). For blocking of activity, cytolytic T cells were incubated for 30 min. at 37° C. with F23.1 antibodies (50 µg/ml). Then $^{51}$Cr-labeled targets were added and the cytolytic assay were performed as described above.

Establishment of Cell Lines and T Cell Clones from Transgenic Mice

Cell lines were made by stimulation of spleen cells with either Con A or allogeneic x-irradiated stimulator cells in medium containing IL-2. After 10 to 14 days, the cells were washed and restimulated ($10^6$ responder cells, $10^7$ x-irradiated stimulator cells) in IL-2-containing medium. Viable cells were obtained by centrifugation over Ficoll. Cloning was carried out by seeding 0.3 cells per well in 96-well microtiter plates containing $10^6$ X-irradiated feeder spleen cells per well and 200 µl of IL-2-containing medium. After 1 to 2 weeks, growing colonies were transferred together with $10^7$ x-irradiated feeder cells into 2 ml of IL-2-containing medium in 24-well Costar plates. From then on, restimulations were carried out at 7-day intervals with $10^6$ cloned cells and 10 x-irradiated stimulators per 1 ml of IL-2-containing culture medium.

Transgenic Mice Express the Introduced T Cell Receptor β Gene

Thirteen pups were born that contained from 1 to about 50 copies of the transgene, according to Southern blot analysis of tail DNA. Of these mice, seven were analyzed after splenectomy for transcription with the oligonucleotide probe that covered the VDJ joining region and that was therefore specific for the transgene. Six of the seven mice showed a 1.3 kb full-length transcript. As observed before for other transgenes, no simple correlation between copy number and transcriptional activity was seen. T lymphocytes obtained from lymph nodes of four transgenic mice were subseguencly analyzed for cell-surface expression of the transgenic β chain on a fluorescence-activated cellsorter (FACS) by using F23.1 antibodies (Table 1). While about 10%–20% of T cells were F23.1-positive in mice 90 and 91, practically all of the T cells from mice 93 and 95 were stained with the F23.1 antibody. This indicates that most, if not all, of the T cells in mice 93 and 95 express the transgenic β chain on the cell surface. Since a background of about 10%–20% F23.1-positive T lymphocytes is expected for these mouse strains (Staers, et al. (1985) *J. Immunol.* 134, 3994–4000), it is unlikely that the transgenic β chain is expressed in mice 90 and 91. In agreement with the FACS analysis, Northern blot analysis did not show any transgene transcription in T lymphocytes of mouse 90 (Table 1).

TABLE 1

Transgenic Mice Express the Introduced T Cell Receptor β Gene

| Founder | Off-spring | Sex[a] | Copy Number[b] | Transgene Tran- scription | T Cell Surface Expression[c] |
|---|---|---|---|---|---|
| 90 | | m | 1 | — | 10%–20% |
| 91 | | f | 20 | ND | 10%–20% |
| 92 | | f | 10 | ND | ND |
| 93 | | f | 5 | + | >98% |
| | 93.1 | m | 0 | ND | ND |
| | 93.2 | m | 20 | + | >98% |
| | 93.4 | m | 2 | + | >98% |
| | 93.9 | f | 20 | + | >98% |
| 94 | | m | 3 | + | ND |
| 95 | | f | 2 | + | >98% |
| | 95.39 | m | 2 | + | ND |
| | 95.40 | m | 2 | ND | ND |

[a] Sex is indicated by m (male) and f (female).
[b] Copy number of the transgene was estimated from signal intensities on Southern blots with PvuII-digested tail DNA hybridized with the Jβ2 probe.
[c] Surface expression of F23.1-positive β chains on lymph node T cells was quantitated by FACS analysis.
ND-Not determined.

Figure 4:
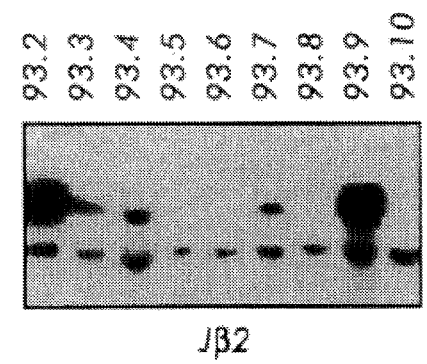
FIG. 4 is a Southern blot analysis of offspring mice derived from a cross of the female transgenic mouse 93 with C57L males.

The male founder mouse 93 was subsequently crossed with female C57L mice (a F23.1-negative mouse strain; Behlke, et al. (1986) *Proc. Natl. Acad. Sci. USA* 83, 767–771. Eighteen offspring mice from the first generation were aalyzed for the inheritance of the transgene by Southern blot hybridization. Three (1 male, 2 females) contained about 20 copies of the transgene, 5 (4 males, 1 female) contained about 2 copies, and 10 lacked the transgene (FIG. 4). This blot shows the anaysis of 9 mice. It demonstrates the inheritance of the transgene (indicated by the 7.7 kb band) in either 2 (mice 93.3, 93.4, 93.7) or 20 (93.2, 93.9) copies. The 5.5 kb band represents the endogenous β locus. Southern blot analysis of Pvull-digested tail DNA was carried out as described with a Jβ2 probe. The segregation of the transgene into 2 and 20 copies could be due to integration of injected DNA into two unlinked chromosomal loci, or could reflect a deletion or amplification event after integration at a single site. Analysis of second generation offspring mice shows that the two different forms of the transgene are stably inherited. The transgene is therefore present in germ-line DNA and transmitted in a Mendelian fashion to both makes and females. Mice with 2 or 20 copies of the transgene were analyzed for cell-surface expression with F23.1 antibodies. Lymph note T cells stimulated in vitro by irradiated allogeneic DBA/2 spleen cells were incubated with Vβ8-specific F23.1 antibodies followed by FITC-labeled sheep anti-mouse immunoglobulin antibodies, and were analyzed on FACS. In parallel, the expression of CD3 molecules was monitored by using the 145.2C11 monoclonal antibody (Leo, et al. (1987) *Proc. Natl. Acad. Sci USA* 84, 1374) followed by FITC-labeled goat anti-hamster immunologlobulin antibody. As shown in FIG. 5, most, if not all, of the peripheral T lymphocytes analyzed in mice 93.2 (20 copies) and 93.4 (2 copies) stain with the Vβ8-specific monoclonal antipody. The staining intensity is similar in both T lymphocyte populations, indicating that despite the difference in copy number, these mice express the transgene to the same extent.

Lymph node cells from mice with 2 copies of the transgene were analyzed for the ratio of CD4- and CD8-positive T cells. Lymph node cells from a transgenic male mouse were 45% $CD4^-$ and 18% $CD8^+$, and from a transgenic female mouse, 35% $CD4^+$ and 29% $CD8^+$; control cells from a C57BL/6 mouse were 45% CD4 and 32% $CD8^+$. These numbers do not deviate significantly from those normally seen. Thus, although the transgenic β chain, derived from a class I-restricted cytotoxic T cell clone, is expressed in most, if not all, of the T lymphocytes, it does not affect the normal ratio of CD4- and CD8-positive T cells.

Transcription of the Transgene is Largely T Cell-Specific

Mouse 93.2, containing 20 copies of transgene was analyzed for tissue-specific expression of the transgene. Northern blot analysis using the VDJ oligonucleotide as a probe reveals strong transcription of the thymus, while little or not transcription is seen in the other tissues analyzed (FIG. 6A). Similar results were obtained for transgenic mice 93.4 and 95.39, containing 2 copies of the transgene (not shown). The small amounts of transcripts we see in some nonlymphoid tissues could be due to infiltrating T lymphocytes or incomplete inactivation of the transgene. N lymphocytes also show a low level of transgene transcription. Both the VDJ oligonucleotide and the Cβ probe identify β chain transcripts in B lymphocytes, while a chain transcripts, even after a longer exposure, are not seen (FIG. 6B). The observed transcripts of the transgene are therefore not due to residual T cell contamination of the B-cell preparation, but reflect an about 20-fold lower level of transgene transcription in B as compared to T lymphocytes.

Transgenic T Lymphocytes Express Only F23.1-Positive β Chains, which Participate in the Formation of Functional Receptors The F23.1 staining experiments indicate that the transgene is expressed in the vast majority of T lymphocytes. It is possible that additional β chains are encoded by endogenous genes. Several independent approaches were used to check this possibility. In a first kind of experiment, membrane extracts from T cells of transgenic mice were "precleared" of Vβ8 proteins by using F23.1 antibodies coupled to Sepharose beads. As shown in FIG. 7, after preclearing, no further β chains were precipitated by a panspecific antiserum (Traunecker, et al. (1986) *Eur. J. Immunol.* 16, 851–854) for mouse β chains. When the original male-specific clone B6.2.16 and T cells from C57BL/6 mice were analyzed for controls, the panspecific antiserum precipitated β chains from the altter but not from the former cells after preclearing with F23.1 antibodies. In a second kind of experiment, T cell receptors were modulated (by capping and endocytosis) by F23.1 antibodies and rabbit anti-mouse immunoglobulin at 37° C. Modulated and nonmodulated cells were then stained with anti-CD3 antibodies (Leo, et al. (1987) supra.). As shown in FIG. 8, modulation with F23.1 antibodies removed all T cell receptor-associated CD3 molecules from cell surfaces of the transgenic mice and from the B6.2.16 clone but not from other T cells. A third kind of experiment showed that the activity of cytolytic T cells from transgenic mice on allogeneic DBA/2 and C3H/HeJ target cells was completely blocked by F23.1 antibodies, whereas those from normal C57BL/6 mice were not inhibited significantly when used on the same targets (FIG. 9). Lysis of allogeneic target cells after in vitro stimulation was specific. Cytolytic T cells from transgenic mice stimulated with DBA/2 cells lysed DBA/2 but not C3H/HeJ target cells, and stimulation with C3H/HeJ cells gave rise to C3H/HeJ-directed, but not DBA/2-directed, killer cells (not shown). Taken together, these experiments indicate that only β chains encoded by the transgene are expressed o T lymphocytes of the transgenic mice and that they are used to form functional T cell receptors.

Endogenouse β Genese are Incompletely Rearranged

Rearrangement of endogenouse β genes can be distinguished from the rearranged transgene by using specific hybridization probes. With a Cβ probe, rearrangements of the Cβ1 locus can be separated from those at the Cβ2 locus (which is present in the transgene) if HindIII-digested T cell DNa is analyzed. This analysis clearly shows that the 9.4 kb germ-line HindIII fragment containing the Cβ1 locus is rearranged in transgenic T lymphocytes frommouse 93.2 (FIG. 10A). The rearrangements, however, appear to be qualitatively different from those seen in normal C57L T lymphocytes used as a control. While no discrete rearranged fragments appear in C57L T cell DNA, a series of fragments (not seen in a B cell control) is evident in T cell and Thymus DNA from trnsgenic mouse 93.2. Also, mouse 93.1, which did not inherit the transgene, looks like the C57L control.

With a probe derived from the 5' flanking region of the Dβ1 gene segment, a series of discrete rearranged fragements is again seen in transgenic but not in control T cell, nor in transgenic B cell, DNA (FIG. 10B). This result shows that partial Dβ1 rearrangements, presumably to Jβ1 and Jβ2 gene segments, are present in unusually high frequencies in the transgenic mouse. Indeed, the sizes of the observed rearranged fragments are in agreement with this assumption. Since these fragments are identified with a 5' flanking probe of Dβ1, they represent partial rearrangements that donot involve Vβ gene segments. Inversion of the Vβ14 gene segment, located downstream of Cβ, would not delete the 5' flanking sequence of Dβ gene segments (Malissen, et al. (1986) Nature 319. 28–33). Analysis of T cell clones from transgenic mice (see below) with a Vβ14 probe, however, shows that endogenouse Vβ14 genese have not been rearranged to Dβ gene segments. In agreement with the Southern blot analysis, a Northern blot analysis of thymus and peripheral T cell RNA with a mixture of $^{32}$P-labeled Vβ7, Vβ9, Vβ11, Vβ12, Vβ14, Vβ15 and Vβ16 gene segments did not reveal Vβ gene transcripts in transgenic mouse 93.2, while a clear signal was obtained with a C57BL/6 control (not shown).

In contrast to the Dβ1 gene segment, the Dβ2 gene segment does not undergo frequent rearrangements in transgenic mouse 93.2. As shown in FIG. 10C, it rather seems that most of the Dβ2 gene segments remain in germ-line configuration in 93.2 thymocytes and T cells. Mouse 93.4, containing only 2 rather than 20 copies of the transgene, shows a similar high frequency of partial Dβ1 rearraangements (not shown). Furthermore, mouse 95.39, independently generated, and a transgenic mouse obtained by coinjection of the same β gene together with a T cell receptor α gene show a predominance of partial Dβ1 rearrangements (not shown). Thus neither the high coy number of the transgene in mouse 93.2 not its peculiar shromosomal location causes this unusual pattern of rearrangement.

The results presented so far do not exclude a low but still significant number of complete endogenous VDJ rearrangements. To obtain a more quantitative estimate, we analyzed nine T cell clones obtained from mice 93.2 and 93.4 with the same Cβ, Dβ1, and Dβ2 probes. Of the 18 endogenouse β loci screened, 13 rearranged Dβ1 to Jβ1, 2 fused Dβ1 with Jβ2, 3 joined Dβ2 with Jβ2, and 2 show unusual rearrangements of both Dβ1 and Dβ2 gene segments that were not further characterized (Table 2). No complete VDJ rearrangements were found, indicating that they occur very rarely if at all.

TABLE 2

T Cells Clones Analyzed

| | | Rearrangements[a] | | | |
|---|---|---|---|---|---|
| Mouse | Clone[b] | Dβ1 to Jβ1 | Dβ1 to Jβ2 | Dβ2 to Jβ1 | Dβ1 to Jβ1[c] |
| 93.2 | 2 | 1 | | 1 | 1 |
| | 8 | 1 | 1 | | |
| | 14 | 1 | | | 1 |
| | 16 | 2[d] | | | |
| | 17 | 2 | | | |
| | 18 | 1 | 1 | | |
| | 19 | 2 | | | |
| | 20[e] | 1 | | 2 | |
| 93.4 | 2 | 2 | | | |

Notes:
[a]Rearrangements of the two homologous loci in each T cell clone were analyzed with Cβ, Dβ1, and Dβ2 probes.
[b]T cell clones were obtained as described in Experimental Procedures.
[c]The sizes of these rearranged fragments do not correspond to those expected for DJ rearrangements.
[d]Indicates that DJ rearrangements have occurred on both homologous chromosomes.
[e]Clone 20 contains one β locus in germ-line configuration.

Expression of the Transgene Regulates Rearrangement of Endogenous β Genes

The majority of endogenous β genes in the transgenic mice show rearrangements of Dβ1 to Jβ1 gene segments. No endogenous VDJ rearrangements are seen. The preponderanve of incomplete Dβ1 to Jβ1 rearrangements is highly unusual, and is independent of the copy number of the transgene and its chromosomal location. It can be deduced from the analysis of T cells and T cell clones that approximately half of the nonproductive β rearrangements in normal T cells represent VDJ rearrangements. Of eight nonfunctional alleles that have been characterized in T cell clones, five show partial DJ rearrangements (at least three of which are Dβ1–Jβ2) and three show aberrant VDJ rearrangements. Expression of the introduced βgene in transgenic mice therefore blocks endogenous β gene rearrangement between D→J and V→DJ joining.

EXAMPLE 2

T Cell Depleted Transgenic Mice

Transgenic mice depleted in T cell population were produced by introducing a transgene encoding the functionally rearranged T cell B receptor chain of Example 1 wherein approximately 90% of the variable region of the β receptor gene was deleted.

Transgene Constructions

The 20 kbp KpnI fragment derived from cosHYβ9-1.14-5 (FIG. 3B) was subcloned in PUC18. This plasmid was deposited with the Centraalbureau Voor Schimmelcultures (CBS) Baarn, The Netherlands on Dec. 5, 1988 and assigned deposit No. CBS726.88. The construction of the deletion transgenes from this plasmid is illustrated schematically in FIGS. 11A, 11B and 12. The functional TCR β gene from the B6.2.16 contains in addition to the fused Vβ8.2, Dβ2 and Jβ2.3 segments the J segments Jβ2.4, Jβ2y and Jβ2.6. A 4.0 kb XbaI fragment contains the VDJ join and the remaining J segments. This fragment was inserted into pSP64 (Promega, Madison, Wis. to form pSP4X). In this region of the KpnI fragment three PstI sites are present, the first at 17 bp from the start of the Vβ8.2 segment, the second between the Jβ2.5 land the Jβ2ψ and the third at 22 bp downstream from the Jβ2ψ segment. The 707 bp located between the first and the last PstI sites were deleted from the KpnI fragment thereby removing all but the first six codons of the Vβ8.2 segment, Dβ2 and Jβ2-Jβ5. Two complementary oligonucleotide sequences were synthesized corresponding to the last six codons of the Jβ2.3 segment and the 34 bp region downstream from the Jβ2.3 segment including the splice donor sequences. The oligomers were prepared in such a way that a PstI site is generated a the border in order to facilitate insertion into a PstI site. Digestion of pSP4X and religation resulted in the pSP2.7XP plasmid carrying a 2.7 kbp XbaI/PstI fragment in which all of the Vβ8.2 sequences, except for the first 17 bp, and the 3' sequences up to the Xba site were deleted. pSP2.7XP was cleaved with PstI and religated in the presence of excess of reannealed oligomers (for sequence data see FIG. 11). The sequence chosen at the 5' and 3' of the oligomers was chosen such, that insertion of reannealed oligomer in the correct orientation restores only the 3' PstI restriction site. Plasmid pSP2.7XP contained one copy of the synthetic of 57 mer in the correct orientation. In the PstI site of pSP2.7XP the 550 bp PstI fragment containing the Jβ2.6 segment derived from the pSP4X subclone was inserted to yield the pSP3.2X* clone. pSP3.2X* carries a 3.2 kb XbaI fragment identical to 4.0 kbp XbaI insert of the pSP4X clone except for the deletion of the 707 bp PstI fragment. Finally, the 4.0 kb XbaI fragment in the 20 kb KpnI fragment was replaced by the 3.2 kb XbaI insert of pSP3.2X* via multiple cloning steps involving the unique SacII site. Such multiple cloning steps are shown in FIG. 12. This resulted in the formation of the ΔV-TCRβ λονε.

A ΔVs-TCRβ clone containing one extra nucleotide was obtained in the same way, except that the pSP2.7XP subclone incorporated oligomers that contained the extra nucleotide in the coding region (FIG. 11). Because of the presence of the additional nucleotide the mRNA transcribed from this construct can not be translated into a polypeptide carrying a C region. This construct served as a control after introduction into transgenic mice. All manipulations involving the deletion of the 707 bp PstI fragment and the insertion of the oligomers were checked by nucleotide sequence analysis.

Generation of Transgenic Mice

The DNA foragments (ΔV-TCRβ or ΔVs-TCRβ) that were used for injection were released from the above vectors using the appropriate restriction endonucleases and purified as described earlier (Krimpenfort, et al. (1988) *Embo. J.* 7, 745). The final DNA concentration was adjusted to 2 µg/ml. Fertilized eggs were recovered in cumulus from the oviducts of superovulated (CBA/BrA×C57B1/LiA) F1 females that had mated with F1 males several hours earlier. The DNA fragments were injected into the most accessible pronucleus of each fertilized egg essentially as described (Hogan, B. J. M., et al. (1985) *Manipulation of the Mouse Embryo: A Laboratory Manual,* Cold Springs Harbor Laboratory Press, Cold Spring Harbor, N.Y.). After overnight culturing two-cell-stage embryos were implanted into the oviducts of pseudopregnant fosters (F1 or BDF) and carried to term. Several weeks after birth total genomic DNA was prepared from tail biopsies as described (Hogan, et al., supra)

DNA Analysis

For Southern blot analysis, 8 µg total genomic DNA was digested with restriction endonucleases as recommended by the supplier, separated on agarose gels and transferred to nitrocellulose. Filters were hybridized to 32P-labeled probes as described (Cuypers, H. T., et al. (1984) *Cell* 37, 141). Final wash was at o.1× SSC, 42° C. The probe used for the transgene analysis was an EcoRI/HincII fragment located downstream from the Jβ2 cluster. This probe recognizes a 6.0 kbp PvuII fragment in germline DNA, whereas a 7.9 kbp PvuII fragment was diagnostic for the ΔV constructs.

RNA Analysis

5–15 µg of total RNA, prepared by the LiCl-urea method (Auffray, C., et al. (1980) *Eur. J. Biochem.* 177, 303) was separated on 1% agarose formaldehyde gels (Maniatis, et al. (1982), supra.) and transferred to nitrocellulose. Probes used for RNA analysis were Cβ probe comprising a cDNA fragment representing the Cβ2 region which also hybridizes with Cβ1 transcripts (Snodgrass, H., et al. (1985) *Nature* 313, 592) and an actin probe (Dodemont, H. J., et al. (1982) *EMBO J.* 1, 167). These probes were 32P-labeled by nick-translation. Hybridization conditions were as described (Cuypers, et al. (1984) *Cell* 37, 141). Final wash was at 0.1× SSC and 60° C.

FACS Analysis

Analysis was performed on a FACS II analyzer (Becton and Dickinson) using established protocols (Scollay, R., et al. (1983) *Thymus* 5, 245). Single cell suspensions were prepared from spleen in balanced salt solution containing 5% fetal calf serum and 0.5 mg/ml sodium azide. Cells were stained with saturating amounts of antibodies and counterstained with FITC-coupled rabbit anti-rat antibodies (Vesmel, W., et al. (1987) *Leukemia* 1 155). The origin and specificity of the antibodies were as follows: L3T4 (monoclonal 129-19 (Pierres, A., et al. (1984) *J. Immunol.* 132, 2775), Thy-1 (monoclonal SgA D2-2), Lyt-2 (monoclonal 53-6-7).

Transgenic Mice

Two transgenic founders were obtained carrying the ΔVs-TCRβ construct. In both transgenic mice multiple copies had integrated in head-to-tail configuration (data not shown). RNA was isolated from spleen of these mice to check transcription of the ΔVs-TCRβ transgene (see below). One ΔVs-TCRβ founder was sacrificed for obduction. No abnormalities were observed (normal thymus, spleen).

Using the ΔV-TCRβ construct eight transgenic mice were generated. In most of these mice multiple copies had integrated. Mouse #1670 (male) did not produce offspring and was sacrificed for analysis. Strikingly, the thymus in this founder was strongly reduced in size. No abnormalities were recorded in other tissues. All transgenic offspring from another transgenic mouse (#1733) had an even more pronounced phenotype as mouse #1670: no thymus was present, whereas other tissues appeared normal. No abnormalities were observed in negative offspring from this transgenic line. Splenocytes from founder 1670 and from positive offspring from #1733 were analyzed by FACS.

Transgene Transcription

As discussed above, the ΔVs-TCRβ differs in only one nucleotide from the ΔV-TCRβ transcripts and therefore does not encode a polypeptide chain containing a TCR constant region.

Two RNA species are transcribed from TCRβ genes, 1.0 kb and 1.3 kb in size. Partially (DJ) rearranged β genes yield the 1.0 kb transcripts, whereas the fully (VDJ) rearranged β genes give rise to the 1.3 kb RNAs. In thymus both TCRB transcripts are present abundantly (Shodgrass, et al. (1985) supra.). In spleen, however, the 1.0 kb TCRB transcript is hardly detectable. Correct transcription and processing of the ΔV gene constructs also lead to a 1.0 kb mRNA. Northern blot analysis using probes specific for the Cβ region cannot discriminate between ΔVs-TCRβ transcripts and DJ transcripts. Therefore, RNA from spleen rather than thymus was chosen for the analysis of the ΔVs-TCRβ transgene expression. RNA was isolated from spleen, from control mice, and from mice carrying the ΔVs-TCRβ construct. As can be concluded form FIG. 13 the endogenous TCRβ gene expression is not affected in the ΔVs-TCRβ transgenic mice. In spleen from control and transgenic mice a 1.3 kb band of approximately equal intensity can be detected with the Cβ probe. This indicates that complete VDJ rearrangements are not inhibited in the ΔVs-TCRβ transgenic mice. However, RNA from the transgenic spleens shows a high expresison of a 1.0 kb RNA species that is probably derived from the transgene ΔVs-TCRβ. The difference in expression level between the two transgenic strains supports this interpretation. We conclude from the RNA analysis, that the ΔVs-TCRβ and therefor probably also the ΔV-TCRβ transgenes give rise to stable transcripts.

Results of FACS Analysis

As it was impossible to isolate a sufficient number o cells from the thymus of the transgenic mice carrying the ΔV-TCRβ construct, FACS analysis was only performed on splenocytes. Splenocytes were isolated from founder #1670 and from transgenic progeny of lines #1673 and #1733. As a control cell suspensions were prepared from the spleen of negative littermates. Splenocytes were stained with anti-sera specific for the B cell marker surface immunoglobylin and the T cell markers Thy-1, L3T4 (T4) and Lyt-2 (T8). The FACS data on cell suspensions from different transgenic mouse lines were essentially the same. In the control cell suspension the B cell specific anti-sera show a reactive and an unrective cell population, representing B and T cells, respectively (FIG. 14). In contrast, in the transgenic cell preparation (1670) all cells stain with the B cell specific anti-sera. This indicates, that all cells in the transgenic spleens are of B cell origin. This observation is supported by the staining patterns obtained with the T cell specific antisera. Whereas in the control spleen approximately 30% of the cells can be stained with the Thy-1 anti-serum, only a minor fraction if any of the transgenic splenocytes are Thy-1 positive. The same observations were made by FACS using the L3T4 and Lyt-2 anti-sera. Apparently, T cells are absent form the spleen of the ΔV-TCRβ transgenic mice.

Conclusion

The RNA analysis of spleen of transgenic mice carrying the ΔVs-TCRβ gene construct shows that the introduced ΔV constructs are highly expressed. Moreover, the ΔVs-TCRβ transgenic mice show, that the transcriptional activity of the ΔV constructs per se does not inhibit the complete rearrangements of the endogenous β chain genes, since in the ΔVs-TCRβ transgenic mice the 1.3 kb VDJ is expressed at similar levels as in control mice. The analysis of the ΔV-TCRβ transgenic mice is still preliminary, e.g. at the moment no data on γδ bearing T cells are available. A few consistent observatons were made: no or only a rudimentary thymic structure was left in several of independent ΔV-TCRβ transgenic mice lines; FACS analysis on splenocytes from these mice demonstrated that T cells were virtually absent. The absence of T cells in the ΔV-TCRβ transgenic mice can be explained in several ways. Firstly, the ΔV transgenic protein itself might be lethal for T cells. This is unlikely, since a high expression of the stucturally similar Dμ-protein is not harmful for A-MuLV transformed pre-B cells. Moreover, it was shown that pre-B cells with a high Dμ-protein expression behave just like B cells that express a complete Ig heavy chain: they proceed in the B cell differentiation pathway with rearrangements of the light chain genes (Reth, et al. (1985) supra.). Seconly, the mutant chain might interfere with T cell maturation. It has been suggested that during thymic maturation T cells are subject to both positive and negative selection processes. These include the stimulation of thymocytes that are able to recognize foreign antigen in association with self MHC as well as the elimination of self-reactive cells. This selection requires the interaction with MHC determinants. TCRs play an essential role in these interactions. In ΔV-TCRβ trnsgenic mice the mutant TCRβ probably prevents expression of the endogenous β chain genes by inhibiting the complete VDJ rearrangements in the same way as the Dμ protein blocks further rearrangements of the Ig heavy chain genes in A-MuLV transformed pre-B cells. Consequently, T cells in these mice do not express a complete β chain gene and therefore do not carry a TCR, that can functionally interact with MHC determinants. As a result all T cells die. Three mechanisms could acocunt for the actual loss of T cells: (i) active deletion of T cells that bear a non-functional TCR; (ii) the deleted TCR transgene forms a receptor complex that is selfreactive and therefore is clonally deleted; (iii) T cells of the ΔV-TCRβ transgenic mice are unable to respond to proliferative stimuli. The available data do not discriminate between these alternatives.

Having described the preferred embodiments of the present invention, it will appear to those ordinarily skilled in the art that various modifications may be made to the disclosed embodiments, and that such modifications are intended to be within the scope of the present invention.

What is claimed is:

1. A transgenic mouse having a phenotype characterized by a disruption of the expression of the Cμ and Cδ portions of the endogenous immunoglobulin heavy chain and an absence of plasma B cells producing naturally occurring mouse antibodies, the phenotype being conferred by an immunoglobulin heavy chain targeting transgene introduced into an ES target cell and integrated into somatic and germ cells of the tranegenic mouse or an ancestor thereof by homologous recombination with a cognate endogenous immunoglobulin heavy chain allele to yield a targeted immunoglobulin heavy chain allele which is not expressed, the immunoglobulin heavy chain targeting transgene comprising a stop codon, DNA sequences for identification and selection of ES cells containing the transgene in the targeted allele and DNA sequences of a mouse heavy chain immunoglobulin gene having sufficient sequence homology to recombine with the endogenous allele in said ES target cell.

2. The transgenic mouse of claim 1, wherein the targeted immunoglobulin heavy chain allele further comprises a deletion of nucleotides from the cognate endogenous immunoglobulin heavy chain allele.

3. The transgenic mouse of claim 2 wherein the deletion of nucleotides from the cognate endogenous immunoglobulin heavy chain allele is a deletion of a portion of the variable region.

4. The tranegenic mouse of claim 1, 2, or 3 wherein the immunoglobulin heavy chain targeting transgene consists essentially of DNA sequences homologous to the endogenous immunoglobulin heavy chain allele, sequences for identification and selection of ES cells containing said transgene in said targeted allele, and a mutation which disrupts expression of the targeted allele wherein the mutation is selected from the group consisting of the insertion of sequences comprising a stop codon, the insertion of sequences resulting in a frameshift, and a deletion of a plurality of nucleotides of the endogenous immunoglobulin heavy chain allele.

5. The transgenic mouse of claim 3, wherein the deletion of nucleotides from the cognate endogenous immunoglobulin heavy chain allele comprises a deletion of J segments of the variable region.

* * * * *

UNITED STATES PATENT AND TRADEMARK OFFICE
CERTIFICATE OF CORRECTION

PATENT NO. : 5,591,669

DATED : January 7, 1997

INVENTOR(S) : Paulus J.A. Krimpenfort and Antonius J.M. Berns

It is certified that error appears in the above-identified patent and that said Letters Patent is hereby corrected as shown below:

Please delete the drawing on the cover page.

Signed and Sealed this

Twenty-fifth Day of March, 1997

Attest:

BRUCE LEHMAN

Attesting Officer     Commissioner of Patents and Trademarks